United States Patent
Kikuchi

(10) Patent No.: US 10,404,953 B2
(45) Date of Patent: Sep. 3, 2019

(54) MULTI-LAYER IMAGE SENSOR, IMAGE PROCESSING APPARATUS, IMAGE PROCESSING METHOD, AND COMPUTER-READABLE RECORDING MEDIUM

(71) Applicant: OLYMPUS CORPORATION, Hachioji-shi, Tokyo (JP)

(72) Inventor: Sunao Kikuchi, Akiruno (JP)

(73) Assignee: OLYMPUS CORPORATION, Tokyo (JP)

(*) Notice: Subject to any disclaimer, the term of this patent is extended or adjusted under 35 U.S.C. 154(b) by 18 days.

(21) Appl. No.: 15/900,721

(22) Filed: Feb. 20, 2018

(65) Prior Publication Data

US 2018/0184055 A1 Jun. 28, 2018

Related U.S. Application Data

(63) Continuation of application No. PCT/JP2015/078953, filed on Oct. 13, 2015.

(51) Int. Cl.
*H04N 9/09* (2006.01)
*H04N 5/33* (2006.01)
(Continued)

(52) U.S. Cl.
CPC .......... *H04N 9/09* (2013.01); *G06T 3/4015* (2013.01); *H04N 5/33* (2013.01);
(Continued)

(58) Field of Classification Search
CPC .. H04N 9/09; H04N 9/04553; H04N 9/04563; H04N 9/04515; H04N 9/646; H04N 9/07; H04N 5/33; G06T 3/4015
(Continued)

(56) References Cited

U.S. PATENT DOCUMENTS

| 2008/0087800 A1* | 4/2008 | Toda ................. H01L 27/14603 250/214 C |
| 2014/0194748 A1 | 7/2014 | Yamamoto et al. |
| 2015/0138412 A1* | 5/2015 | Ovsiannikov .......... H04N 9/045 348/302 |

FOREIGN PATENT DOCUMENTS

| JP | 2007329227 A | 12/2007 |
| JP | 2007329380 A | 12/2007 |

(Continued)

OTHER PUBLICATIONS

International Search Report (ISR) dated Nov. 17, 2015 issued in International Application No. PCT/JP2015/078953.
(Continued)

*Primary Examiner* — Allen C Wong
(74) *Attorney, Agent, or Firm* — Holtz, Holtz & Volek PC

(57) ABSTRACT

A multi-layer image sensor includes: a first image sensor including a first pixel and a second pixel; and a second image sensor including a third pixel and at least one of a fourth pixel and a fifth pixel. The second image sensor has a light receiving surface where the first image sensor is stacked. At least a portion of the fourth pixel is arranged at a position corresponding to a position of the first pixel and at a position overlapping with the first pixel in a stacking direction of the first sensor. At least a portion of the third pixel is arranged at a position corresponding to a position of the second pixel and at a position overlapping with the second pixel in the stacking direction of the first sensor.

23 Claims, 16 Drawing Sheets

(51) Int. Cl.
  *H04N 9/07*  (2006.01)
  *G06T 3/40*  (2006.01)
  *H04N 9/64*  (2006.01)
  *H04N 9/04*  (2006.01)

(52) U.S. Cl.
  CPC ..... *H04N 9/04515* (2018.08); *H04N 9/04553* (2018.08); *H04N 9/04563* (2018.08); *H04N 9/07* (2013.01); *H04N 9/646* (2013.01)

(58) Field of Classification Search
  USPC ........................................................ 348/164
  See application file for complete search history.

(56) References Cited

FOREIGN PATENT DOCUMENTS

| | | |
|---|---|---|
| JP | 2013121132 A | 6/2013 |
| JP | 2014135535 A | 7/2014 |

OTHER PUBLICATIONS

Written Opinion dated Nov. 17, 2015 issued in International Application No. PCT/JP2015/078953.

* cited by examiner

MULTI-LAYER IMAGE SENSOR, IMAGE PROCESSING APPARATUS, IMAGE PROCESSING METHOD, AND COMPUTER-READABLE RECORDING MEDIUM

CROSS-REFERENCE TO RELATED APPLICATION

This application is a continuation of International Application No. PCT/JP2015/078953, filed on October 13, 2015, the entire contents of which are incorporated herein by reference.

BACKGROUND

1. Technical Field

The disclosure relates to a multi-layer image sensor, an image processing apparatus, an image processing method, and a computer-readable recording medium.

2. Related Art

In the related art, there is a known technique for capturing a visible light image and an infrared light image simultaneously by an imaging apparatus. For example, JP 2014-135535 A discloses a technique for simultaneously capturing a visible light image and an infrared light image by stacking an image sensor capable of capturing a visible light image onto an image sensor capable of capturing an infrared light image in an optical axis direction.

In addition, JP 2013-121132 A discloses a technique for simultaneously capturing a visible light image and an infrared light image by arranging a color filter for visible light capturing and an infrared filter for infrared capturing in a mosaic pattern on one image sensor.

Meanwhile, the color filter for visible light capturing provided in each of pixels of the conventional image sensor has sensitivity in the infrared light band in addition to the visible light band, leading to deterioration of the color reproducibility of the visible light image. To cope with this, the conventional image sensor provides with an infrared cutoff filter to cut off the infrared light on a light receiving surface of the image sensor to prevent deterioration of the color reproducibility of the visible light image.

In contrast, due to the configuration of simultaneously capturing the visible light image and the infrared light image in the above-described JP 2014-135535 A and JP 2013-121132 A, it is difficult to provide the infrared cutoff filter on the light receiving surface of the image sensor. To overcome this issue, the above-described JP 2014-135535 A subtracts infrared light information included in the visible light image captured by an upper-layer image sensor using infrared light information included in the infrared light image captured by a lower-layer image sensor so as to prevent the deterioration of the color reproducibility of the visible light image.

JP 2013-121132 A subtracts a pixel value of an infrared light image from a pixel value of a visible light image to prevent the deterioration of the color reproducibility of the visible light image.

SUMMARY

In some embodiments, a multi-layer image sensor includes: a first image sensor including: a first pixel having sensitivity in a visible light band and having sensitivity of a first predetermined value or more at a boundary between the visible light band and an infrared light band; and a second pixel having sensitivity in the visible light band and having sensitivity less than the first predetermined value at the boundary between the visible light band and the infrared light band, the first and second pixels being arranged in a two-dimensional matrix, the first image sensor being configured to receive light and perform photoelectric conversion to generate first image data; and a second image sensor including: a third pixel having sensitivity in an infrared light band; and at least one of a fourth pixel and a fifth pixel, the fourth pixel having sensitivity in a visible light band and having sensitivity of a second predetermined value or more at a boundary between the visible light band and an infrared light band, the fifth pixel having sensitivity in the visible light band and having sensitivity less than the second predetermined value at the boundary between the visible light band and the infrared light band, the third pixel and the at least one of the fourth pixel and the fifth pixel being arranged in a two-dimensional matrix, the second image sensor being configured to receive light and perform photoelectric conversion to generate second image data. The second image sensor has a light receiving surface where the first image sensor is stacked. At least a portion of the fourth pixel included in the second image sensor is arranged at a position corresponding to a position of the first pixel included in the first image sensor and at a position overlapping with the first pixel in a stacking direction of the first sensor. At least a portion of the third pixel included in the second image sensor is arranged at a position corresponding to a position of the second pixel included in the first image sensor and at a position overlapping with the second pixel in the stacking direction of the first sensor.

In some embodiments, a multi-layer image sensor includes: a first image sensor including: a first pixel having sensitivity in a visible light band and having sensitivity of a predetermined value or more at a boundary between the visible light band and an infrared light band; and a second pixel having sensitivity in the visible light band and having sensitivity less than the predetermined value at the boundary between the visible light band and the infrared light band, the first and second pixels being arranged in a two-dimensional matrix, the first image sensor being configured to receive light and perform photoelectric conversion to generate first image data; and a second image sensor including: a third pixel having sensitivity in a infrared light band; and at least one of the fourth pixel and the fifth pixel, the fourth pixel having sensitivity in a visible light band and having sensitivity of a second predetermined value or more at a boundary between the visible light band and an infrared light band, the fifth pixel having sensitivity in the visible light band and having sensitivity less than the second predetermined value at the boundary between the visible light band and the infrared light band, the third pixel and the at least one of the fourth pixel and the fifth pixel being arranged in a two-dimensional matrix, the second image sensor being configured to receive light and perform photoelectric conversion to generate second image data. The second image sensor has a light receiving surface where the first image sensor is stacked. At least a portion of the fifth pixel included in the second image sensor is arranged at a position corresponding to a position of the second pixel included in the first image sensor and at a position overlapping with the second pixel in a stacking direction of the first sensor. At least a portion of the third pixel included in the second image sensor is arranged at a position corresponding to a position of the first pixel included in the first image sensor and at a position overlapping with the first pixel in the stacking direction of the first sensor.

In some embodiments, an image processing apparatus includes: an acquisition unit configured to obtain each of the first image data and the second image data generated by one of the above-described multi-layer image sensors; an interpolation image generation unit configured to: generate a first interpolation image interpolating the first pixel of the first image sensor and a second interpolation image interpolating the second pixel of the first image sensor, based on the first image data obtained by the acquisition unit; and generate a third interpolation image interpolating the at least one of the fourth pixel and the fifth pixel of the second image sensor and a fourth interpolation image interpolating the third pixel of the second image sensor, based on the second image data obtained by the acquisition unit; and a color correction processing unit configured to perform color correction of the first interpolation image and the second interpolation image, based on the third interpolation image and the fourth interpolation image generated by the interpolation image generation unit.

In some embodiments, an image processing method includes: obtaining each of the first image data and the second image data generated by one of the above-described multi-layer image sensors; generating a first interpolation image interpolating the first pixel of the first image sensor and a second interpolation image interpolating the second pixel of the first image sensor, based on the obtained first image data; generating a third interpolation image interpolating the at least one of the fourth pixel and the fifth pixel of the second image sensor and a fourth interpolation image interpolating the third pixel of the second image sensor, based on the obtained second image data; and performing color correction of the first interpolation image and the second interpolation image, based on the generated third interpolation image and the generated fourth interpolation image.

In some embodiments, provided is a non-transitory computer-readable recording medium with an executable program stored thereon. The program causes an image processing apparatus to execute: obtaining each of the first image data and the second image data generated by one of the above-described multi-layer image sensors; generating a first interpolation image interpolating the first pixel of the first image sensor and a second interpolation image interpolating the second pixel of the first image sensor, based on the obtained first image data; generating a third interpolation image interpolating the at least one of the fourth pixel and the fifth pixel of the second image sensor and a fourth interpolation image interpolating the third pixel of the second image sensor, based on the obtained second image data; and performing color correction of the first interpolation image and the second interpolation image, based on the generated third interpolation image and the generated fourth interpolation image.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 22 is a diagram schematically illustrating a configuration of a first image sensor according to a third modification of the embodiment of the disclosure;

FIG. 23 is a diagram schematically illustrating a configuration of a second image sensor according to the third modification of the embodiment of the disclosure;

DETAILED DESCRIPTION

Figure 1:
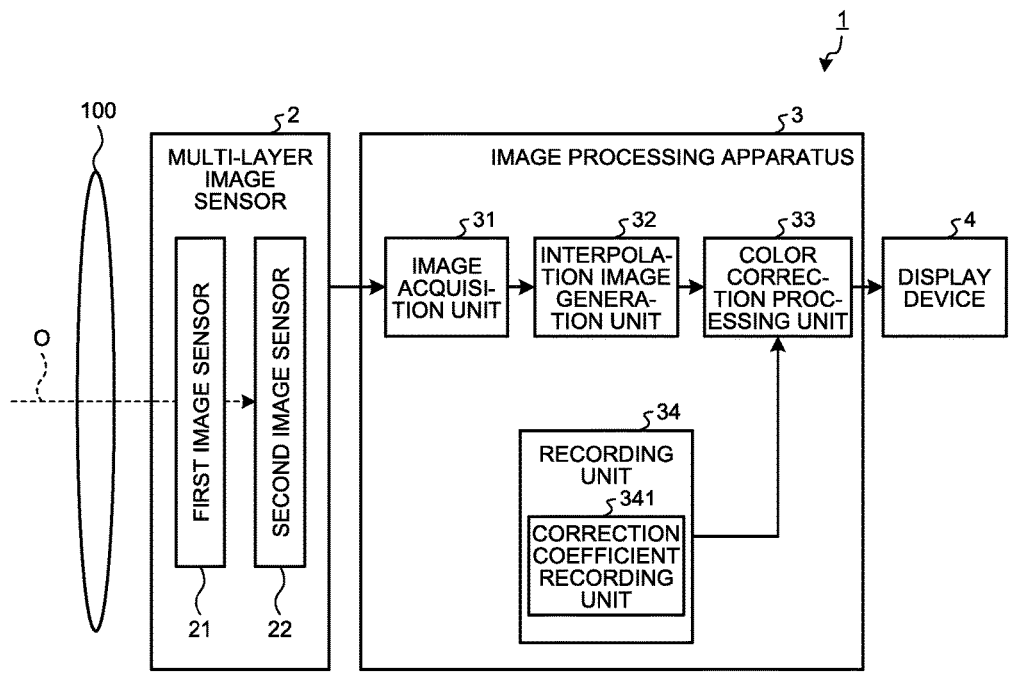
FIG. 1 is a block diagram illustrating a functional configuration of an imaging system according to a first embodiment of the disclosure.

Hereinafter, an imaging system including a multi-layer image sensor will be described according to embodiments of the disclosure (hereinafter, referred to as "embodiment(s)"). Note that the disclosure is not intended to be limited by these embodiments. In the description of the drawings, the same portions are given the same reference numerals. Furthermore, it needs to be kept in mind that the drawings are schematic, and the relationship between the thickness and the width of individual members and the ratio between the members are different from an actual case. Still further, there are portions having different dimensions and ratios even between the drawings.

First Embodiment

Configuration of Imaging System

FIG. 1 is a block diagram illustrating a functional configuration of an imaging system according to a first embodiment of the disclosure. An imaging system 1 illustrated in FIG. 1 includes: an optical system 100 that forms a subject image on a multi-layer image sensor 2; the multi-layer image sensor 2 formed by stacking mutually different image sensors and configured to capture the subject image formed by the optical system 100 and generate image data of the subject image; an image processing apparatus 3 that performs image processing on the image data generated by the multi-layer image sensor 2 and outputs the processed image data to the outside; and a display device 4 that displays an image corresponding to the image data that has undergone image processing by the image processing apparatus 3.

The optical system 100 includes one or more lenses, or the like. The optical system 100 is provided movably along an optical axis O and forms a subject image on a light receiving surface of the multi-layer image sensor 2.

Configuration of Multi-layer Image Sensor

Figure 2:
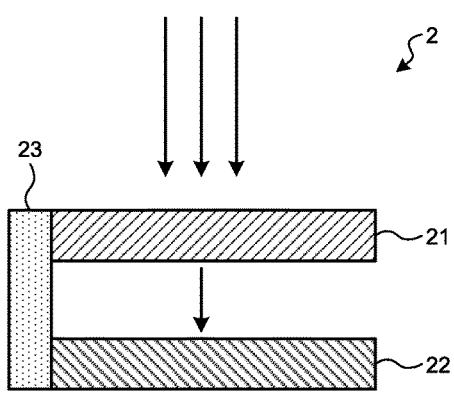
FIG. 2 is a diagram schematically illustrating a cross section of a multi-layer image sensor in FIG. 1.

Next, a configuration of the multi-layer image sensor 2 will be described. FIG. 2 is a diagram schematically illustrating a cross section of the multi-layer image sensor 2. As illustrated in FIG. 2, the multi-layer image sensor 2 includes a first image sensor 21 (a first substrate), a second image sensor 22 (a second substrate), and a connecting portion 23 connecting the first image sensor 21 with the second image sensor 22. The multi-layer image sensor 2 has the first image sensor 21 being stacked (overlaid) on the light receiving surface side of the second image sensor 22 via the connecting portion 23, with the first and second image sensors 21 and 22 being electrically connected via the connecting portion 23. Specifically, the multi-layer image sensor 2 has the first image sensor 21 and the second image sensor 22 being stacked in a direction along the optical axis direction O (vertical direction) of the optical system 100.

The first image sensor 21 includes a plurality of pixels arranged in a two-dimensional matrix to receive light and perform photoelectric conversion to generate image signals. In addition, the first image sensor 21 includes a plurality of visible light filters each having a mutually different maximum value of the transmission spectrum in the visible light band. Specifically, the first image sensor 21 includes: a first pixel having sensitivity in a visible light band and having sensitivity of a predetermined value or more at a boundary between the visible light band and an infrared light band; and a second pixel having sensitivity in the visible light band and having sensitivity less than the predetermined value at a boundary between the visible light band and the infrared light band, the pixels being arranged in a two-dimensional matrix. Herein, the sensitivity of the predetermined value or more is, for example, a sensitivity of a half value of the maximum value of sensitivity, or more.

Figure 3:
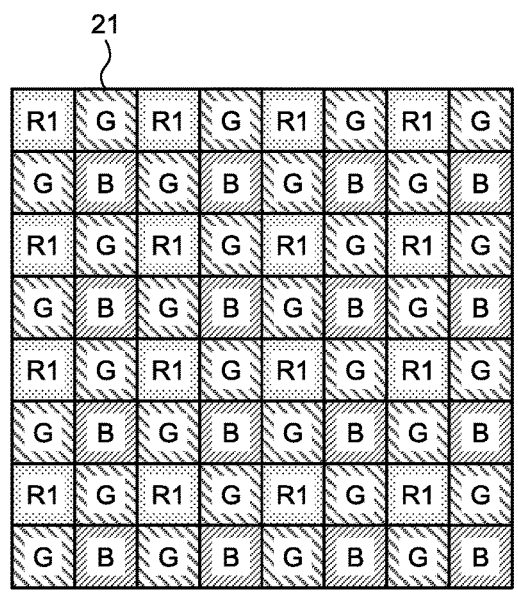
FIG. 3 is a diagram schematically illustrating a configuration of a first image sensor according to the first embodiment of the disclosure.

FIG. 3 is a diagram schematically illustrating a configuration of the first image sensor 21. As illustrated in FIG. 3, the first image sensor 21 includes: the first pixel having sensitivity in the visible light band and having sensitivity of a predetermined value or more at a boundary between the visible light band and the infrared light band; and the second pixel having sensitivity in the visible light band and having sensitivity less than a predetermined value at a boundary between the visible light band and the infrared light band, the pixels being arranged in a two-dimensional matrix. Specifically, the first image sensor 21 forms a predetermined array pattern (Bayer pattern) using a filter R1, a filter G, and a filter B, having mutually different maximum values of the transmission spectrum in the visible light band, with each of color filters forming this array pattern being arranged at a position corresponding to any of the plurality of pixels. In the following, the pixel including each of the filter R1, the filter G, and the filter B on the light receiving surface will be expressed as a pixel R1, a pixel G, and a pixel B, respectively. In the first embodiment, the pixel R1 functions as the first pixel of the first image sensor 21 and the pixels G and B function as the second pixels of the first image sensor 21.

Figure 4:
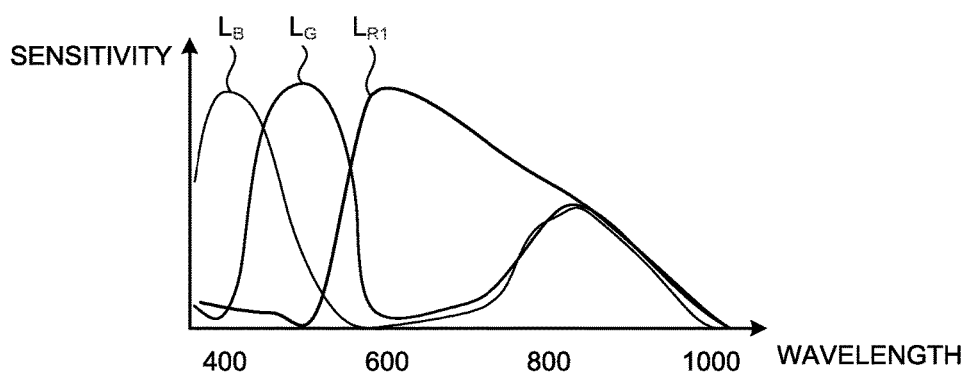
FIG. 4 is a diagram illustrating an exemplary sensitivity characteristic of each of pixels of the first image sensor according to the first embodiment of the disclosure.

FIG. 4 is a diagram illustrating an exemplary sensitivity characteristic of each of the pixels of the first image sensor 21. In FIG. 4, the horizontal axis represents the wavelength (nm) and the vertical axis represents the sensitivity. In FIG. 4, a curve $L_{R1}$ illustrates a sensitivity characteristic of the pixel R1, a curve $L_B$ illustrates a sensitivity characteristic of the pixel B, and a curve $L_G$ illustrates a sensitivity characteristic of the pixel G. In FIG. 4, in order to simplify the description, sensitivity characteristics of the individual pixels will be described.

As illustrated by the curve $L_{R1}$ in FIG. 4, the pixel R1 has a maximum value of sensitivity in the wavelength band of visible light. Specifically, the pixel R1 has the maximum value of sensitivity in the wavelength band of visible light of 620 nm to 750 nm and also has sensitivity to a portion of the light in the wavelength band of infrared light of 750 nm to 950 nm. That is, the pixel R1 functions as a first pixel having sensitivity of a predetermined value or more at a boundary between the visible light band and the infrared light band. As illustrated by the curve $L_G$ in FIG. 4, the pixel G has a maximum value of sensitivity in the wavelength band of visible light of 495 nm to 570 nm and also has sensitivity to a portion of the light in the wavelength band of infrared light of 750 nm to 950 nm. Furthermore, as illustrated by the curve $L_B$ in FIG. 4, the pixel B has a maximum value of sensitivity in the wavelength band of visible light of 400 to 550 nm and also has sensitivity to a portion of the light in the wavelength band of infrared light of 750 nm to 950 nm. That is, each of the pixel G and the pixel B functions as a second pixel having sensitivity in the visible light band and having sensitivity less than a predetermined value at the boundary between the visible light band and the infrared light band.

Returning to FIG. 2, the configuration of the multi-layer image sensor 2 will be continuously described.

The second image sensor 22 includes a plurality of pixels arranged in a two-dimensional matrix to receive light transmitted through the first image sensor 21 and perform photoelectric conversion to generate image signals. In addition, the second image sensor 22 includes a visible light filter having a maximum value of the transmission spectrum within the visible light band and an infrared light filter transmitting the visible light and the infrared light. Specifically, the second image sensor 22 includes: a third pixel having sensitivity in the infrared light band; and at least one of a fourth pixel and a fifth pixel, the fourth pixel having sensitivity in the visible light band and having sensitivity of a predetermined value or more at a boundary between the visible light band and the infrared light band, the fifth pixel having sensitivity in the visible light band and having sensitivity less than a predetermined value at a boundary between the visible light band and the infrared light band, the pixels being arranged in a two-dimensional matrix.

Figure 5:
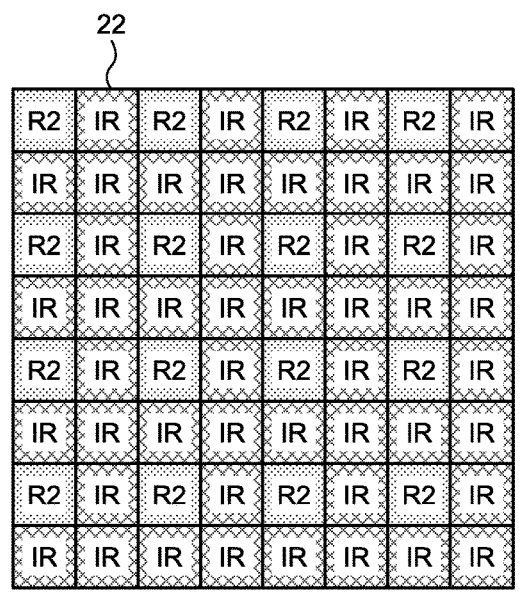
FIG. 5 is a diagram schematically illustrating a configuration of a second image sensor according to the first embodiment of the disclosure.

FIG. 5 is a diagram schematically illustrating a configuration of the second image sensor 22. As illustrated in FIG. 5, the second image sensor 22 includes: the fourth pixel having sensitivity in the visible light band and having sensitivity of a predetermined value or more at a boundary between the visible light band and the infrared light band; and the third pixel having sensitivity in the infrared light band, the pixels being arranged in a two-dimensional matrix. Specifically, the second image sensor 22 uses a filter R2 having a maximum value of the transmission spectrum within the wavelength band of visible light and a filter IR that transmits light in each of the wavelength band of visible light and the wavelength band of infrared light to form a predetermined array pattern. Each filter forming this array pattern is arranged at a position corresponding to any of the plurality of pixels. In the following, the pixel including each of the filter R2 and the filter IR on the light receiving surface will be expressed as a pixel R2 and a pixel IR, respectively. Furthermore, the light receiving surface of the pixel R2 includes an infrared cutoff filter to cut off the wavelength band of infrared light. At least a portion of the pixels R2 included in the second image sensor 22 is arranged at a position corresponding to the position of the pixel R1 (first pixel) included in the first image sensor 21 and at a position overlapping with the pixel R1 in a stacking direction (optical axis direction O). Furthermore, at least a portion of the pixels IR included in the second image sensor 22 is arranged at a position corresponding to any of the positions of the pixel B (second pixel) and the pixel G (second pixel) included in the first image sensor 21 and at a position overlapping with any of the pixel B and the pixel G in the stacking direction (optical axis direction O).

Figure 6:
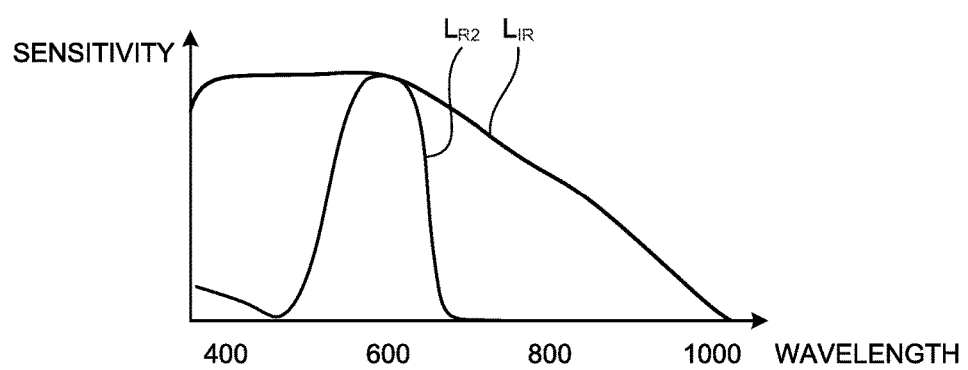
FIG. 6 is a diagram illustrating an exemplary sensitivity characteristic of each of pixels of the second image sensor according to the first embodiment of the disclosure.

FIG. 6 is a diagram illustrating an exemplary sensitivity characteristic of each of the pixels of the second image sensor 22. In FIG. 6, the horizontal axis represents the wavelength (nm) and the vertical axis represents the sensitivity. In FIG. 6, a curve $L_{R2}$ illustrates a sensitivity characteristic of the pixel R2, and a curve $L_{IR}$ illustrates a sensitivity characteristic of the pixel IR. In FIG. 6, in order to simplify the description, sensitivity characteristics of the individual pixels will be described.

As illustrated by the curve $L_{R2}$ in FIG. 6, the pixel R2 has a maximum value of sensitivity in the wavelength band of visible light. Specifically, the pixel R2 has the maximum value of sensitivity in the wavelength band of visible light of 580 nm to 620 nm. That is, the pixel R2 has sensitivity in the wavelength band of visible light alone. Moreover, as illustrated by the curve $L_{IR}$ in FIG. 6, the pixel IR has sensitivity in each of the wavelength bands of visible light and infrared light.

In the above-configured multi-layer image sensor 2, the first image sensor 21 has a small thickness of about several μm, and thus transmits a portion of the light incident from the light receiving surface of each of pixels. The transmitted light is incident on the light receiving surface side of the second image sensor 22 provided as a lower layer of the first image sensor 21. The light absorption rate for individual depths of the silicon forming the first image sensor 21 varies with wavelength. Accordingly, a shallow portion of the silicon of the first image sensor 21 has a high absorption rate for the light having a short wavelength, while having a low absorption rate for the light having a long wavelength. That is, the shorter the wavelength of light, the less the light transmitted from the first image sensor 21, while the longer the wavelength of light, the more the light transmitted from the first image sensor 21. Therefore, the wavelength of light transmitted through the first image sensor 21 can be changed by appropriately adding modification including a design change to the first image sensor 21. In the first embodiment, the light having a wavelength longer than 600 nm is described as being transmitted through the first image sensor 21. That is, the boundary between the visible light band and the infrared light band is described as being 600 nm.

Figure 7:
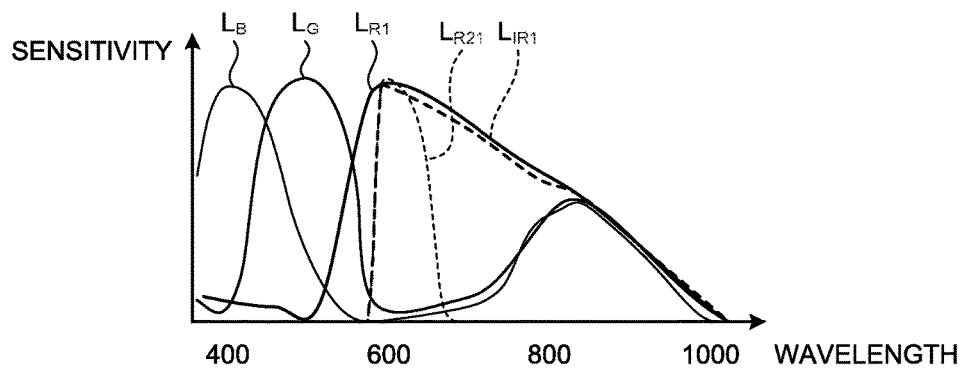
FIG. 7 is a diagram illustrating an exemplary sensitivity characteristic of each of pixels in a case where the first image sensor is stacked on the second image sensor according to the first embodiment of the disclosure.

FIG. 7 is a diagram illustrating an exemplary sensitivity characteristic of each of pixels in a case where the first image sensor 21 is stacked on the second image sensor 22. In FIG. 7, the horizontal axis represents the wavelength (nm) and the vertical axis represents the sensitivity. In FIG. 7, the curve $L_{R1}$ illustrates a sensitivity characteristic of the pixel R1, the curve $L_B$ illustrates a sensitivity characteristic of the pixel B, the curve $L_G$ illustrates a sensitivity characteristic of the pixel G, a curve $L_{R21}$ illustrates a sensitivity characteristic of the pixel R2 in a case where the first image sensor 21 is stacked on the second image sensor 22, and a curve $L_{IR1}$ illustrates a sensitivity characteristic of the pixel IR in a case where the first image sensor 21 is stacked on the second image sensor 22.

As illustrated in FIG. 7, the light having a short wavelength is absorbed by the first image sensor 21, and thus, the second image sensor 22 cannot receive light having a short wavelength. Therefore, as illustrated by the curves $L_{R21}$ and $L_{IR1}$, each of the pixel R2 and the pixel IR has no sensitivity to a wavelength of 600 nm or less.

[Configuration of Image Processing Apparatus]

Returning to FIG. 1, a configuration of the image processing apparatus 3 will be described.

The image processing apparatus 3 includes an image acquisition unit 31, an interpolation image generation unit 32, a color correction processing unit 33, and a recording unit 34.

The image acquisition unit 31 obtains each of first image data generated by the first image sensor 21 and second image data generated by the second image sensor 22 in the multi-layer image sensor 2, and outputs the obtained image data to the interpolation image generation unit 32.

The interpolation image generation unit 32 performs interpolation processing of interpolating pixels of each of the pixels R1, G, and B toward the first image data generated by the first image sensor 21 and input from the image acquisition unit 31 to generate interpolation image data of each of colors, and outputs the generated interpolation image data to the color correction processing unit 33. For example, the interpolation image generation unit 32 extracts edge information of the pixel G and performs known interpolation processing using a method of discriminating the direction of the extracted edge information and a color difference component to generate interpolation image data of each of the colors. The interpolation image generation unit 32 performs interpolation processing of interpolating pixels of each of the pixel R2 and pixel IR toward the second image data generated by the second image sensor 22 and input from the image acquisition unit 31 to generate interpolation image data of the pixel R2 and the pixel IR, and outputs the generated interpolation image data to the color correction processing unit 33. For example, the interpolation image generation unit 32 generates interpolation image data of each of the pixel R2 and the pixel IR by performing known bilinear interpolation processing, bicubic interpolation processing, or the like.

On the basis of a correction coefficient recorded in a correction coefficient recording unit 341 of the recording unit 34 to be described below, the color correction processing unit 33 corrects a pixel value of a target pixel of the interpolation image corresponding to each of interpolation image data input from the interpolation image generation unit 32, and outputs a correction result to the display device 4.

The recording unit 34 is formed with a volatile memory, a nonvolatile memory, or the like, and records various types of information of the image processing apparatus 3. The recording unit 34 also includes the correction coefficient recording unit 341 to record a correction coefficient to be used by the color correction processing unit 33 to correct the pixel value of the target pixel of the interpolation image. Herein, the correction coefficient is a coefficient obtained in advance by results of experiments and simulation. In the first embodiment, it is a matrix of 3 rows and 5 columns.

Configuration of Display Device

Next, the display device 4 will be described.

The display device 4 displays an image that corresponds to the image data image-processed by the image processing apparatus 3. The display device 4 is formed with a display panel of liquid crystal, organic electroluminescence (EL), or the like.

Operation of Image Processing Apparatus

Figure 8:
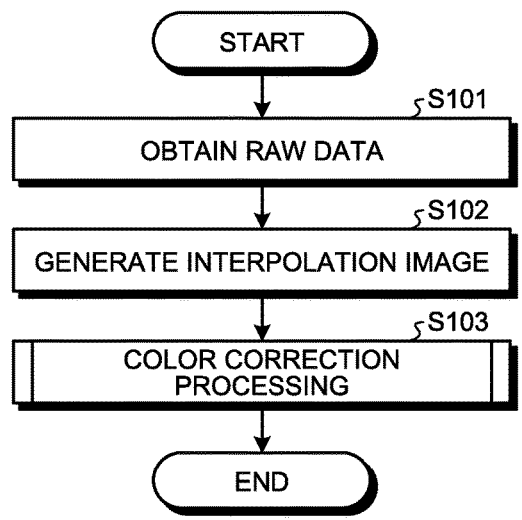
FIG. 8 is a flowchart illustrating outline of processing executed by an image processing apparatus according to the first embodiment of the disclosure.
Figure 9:
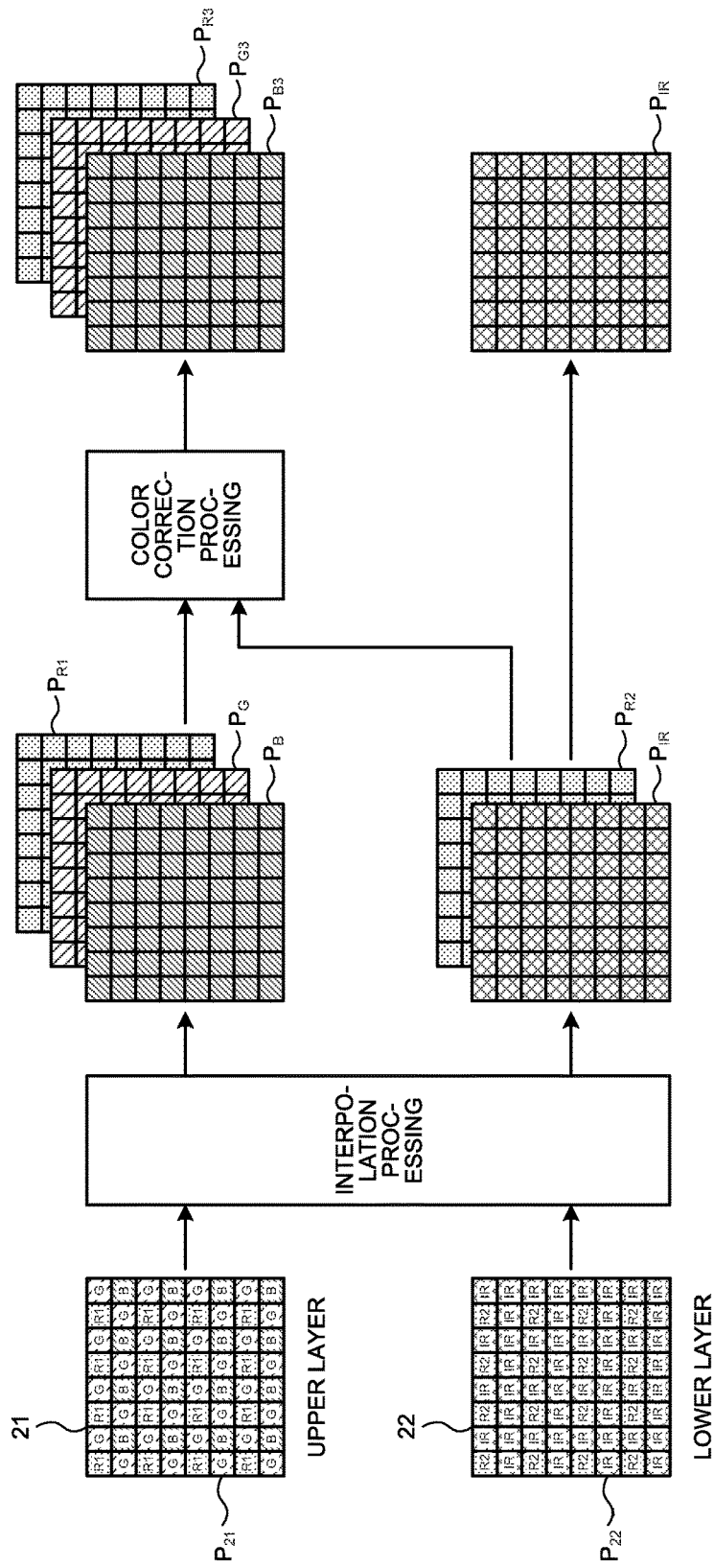
FIG. 9 is a schematic diagram illustrating outline of processing executed by the image processing apparatus according to the first embodiment of the disclosure.

Next, operation of the image processing apparatus 3 will be described. FIG. 8 is a flowchart illustrating an outline of processing executed by the image processing apparatus 3. FIG. 9 is a schematic diagram illustrating an outline of processing executed by the image processing apparatus 3.

As illustrated in FIG. 8, first, the image acquisition unit 31 obtains each of the first image data and the second image data as RAW data generated by the multi-layer image sensor 2 (Step S101). Specifically, as illustrated in FIG. 9, the image acquisition unit 31 obtains a first image P21 corresponding to the first image data generated by the upper-layer first image sensor 21 and a second image P22 generated by the lower-layer second image sensor 22 from the multi-layer image sensor 2.

Subsequently, the interpolation image generation unit 32 generates an interpolation image corresponding to the interpolation image data for each of the first image P21 and the second image P22 obtained by the image acquisition unit 31 (Step S102). Specifically, as illustrated in FIG. 9, the interpolation image generation unit 32 performs interpolation processing of interpolating each of the pixel R1, the pixel G, and the pixel B toward the first image P21 obtained by the image acquisition unit 31 to generate an interpolation image $P_{R1}$, an interpolation image $P_G$ and an interpolation image $P_B$ corresponding to the interpolation image data of each of the colors. For example, the interpolation image generation unit 32 extracts edge information from the pixel value of the first image P21 and interpolates each of the pixel R1, the pixel G, and the pixel B to generate the interpolation image $P_{R1}$, the interpolation image $P_G$ and the interpolation image $P_B$ for individual colors on the basis of the extracted edge information. Furthermore, the interpolation image generation unit 32 performs interpolation processing of interpolating each of the pixel R2 and the pixel IR toward the second image P22 obtained by the image acquisition unit 31 to generate an interpolation image $P_{R2}$ and an interpolation image $P_{IR}$ for each of the pixel R2 and the pixel IR. In a case where the imaging system 1 displays the infrared light image alone on the display device 4, the image processing apparatus 3 outputs the interpolation image $P_{IR}$ to the display device 4. This enables the display device 4 to display the infrared light image. In this case, it is possible to appropriately change the display mode, that is, the display device 4 may superimpose the infrared light image on a visible light image generated by processing described below, or may display the infrared light image alone as a monochrome image.

Thereafter, the color correction processing unit 33 uses the interpolation image generated by the interpolation image generation unit 32 to perform color correction processing for each of the pixels (Step S103).

Color Correction Processing

Figure 10:
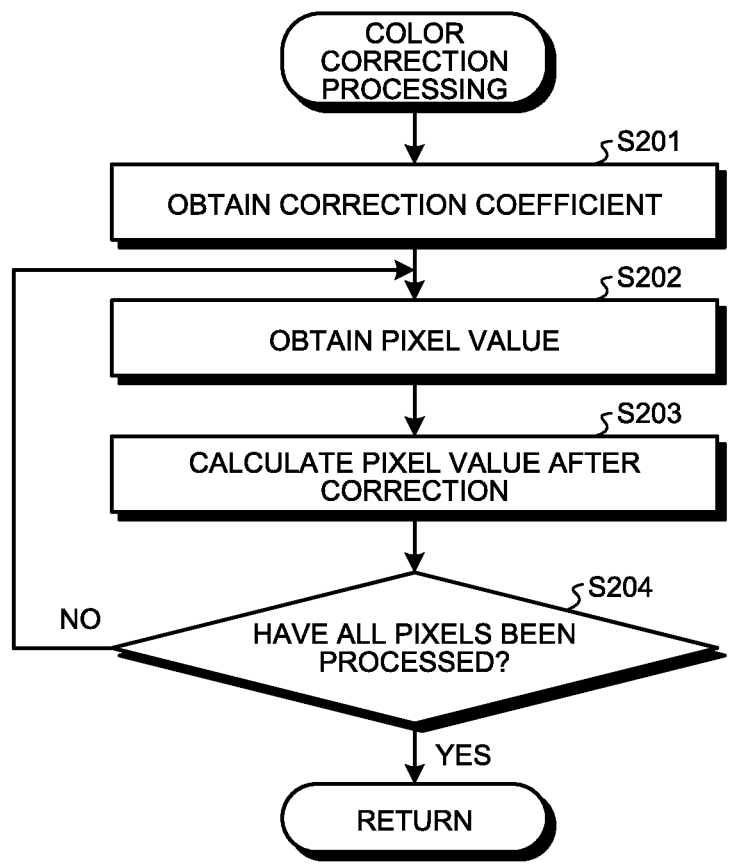
FIG. 10 is a flowchart illustrating an outline of color correction processing in FIG. 8.

FIG. 10 is a flowchart illustrating an outline of color correction processing of Step S103 in FIG. 8.

As illustrated in FIG. 10, the color correction processing unit 33 first obtains a correction coefficient from the correction coefficient recording unit 341 (Step S201), and then obtains a pixel value of the target pixel in the interpolation image generated by the interpolation image generation unit 32 (Step S202).

Subsequently, the color correction processing unit 33 calculates a corrected pixel value using the pixel value of the target pixel obtained in Step S202, the correction coefficient obtained in Step S201, and Formula (1) (Step S203).

$$\begin{bmatrix} R \\ G \\ B \end{bmatrix} = T_{3\times 5} \begin{bmatrix} Ri \\ Gi \\ Bi \\ R_L \\ IR \end{bmatrix} \quad (1)$$

In Formula (1), each of R, G, and B represents a pixel value after color correction, T represents a correction coefficient, and each of Ri, Gi, and Bi represents a pixel value of an interpolation image obtained by interpolating the first image data generated by the first image sensor 21 including IR information, $R_L$ represents a pixel value of an interpolation image obtained by interpolating the second image data generated by the second image sensor 22, and IR represents a pixel value of the pixel IR.

Thereafter, in a case where the color correction of all the pixels of the interpolation image generated by the interpolation image generation unit 32 is finished (Step S204: Yes), the image processing apparatus 3 returns to FIG. 8 and ends the present processing. With this processing, as illustrated in FIG. 9, the color correction processing unit 33 generates each of the image $P_{R3}$, the image $P_{G3}$, and the image $P_{B3}$ obtained by removing IR information (IR component) from each of the interpolation image $P_{R1}$, the interpolation image $P_G$ and the interpolation image $P_B$.

Figure 11:
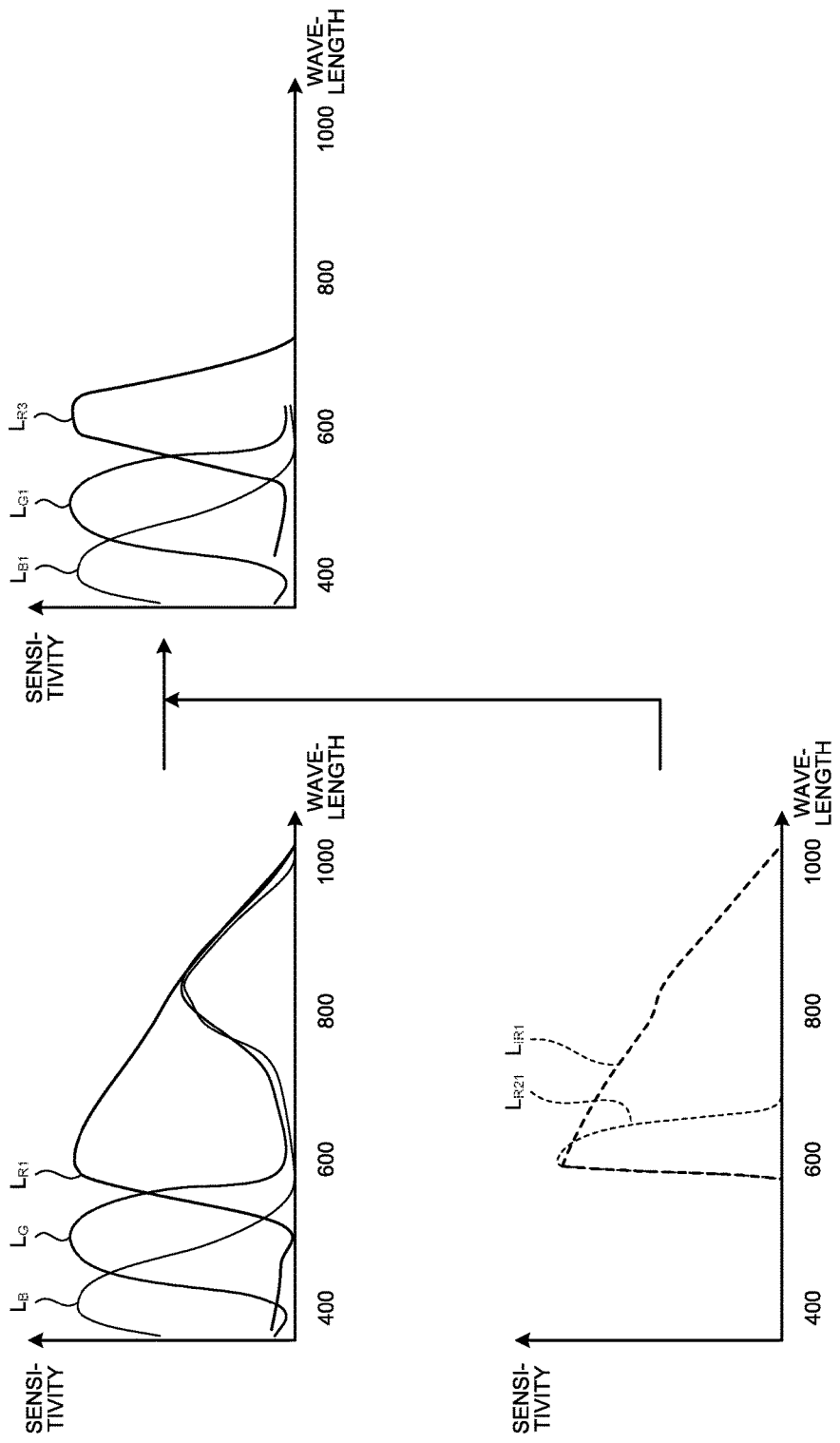
FIG. 11 is a schematic diagram illustrating outline of color correction executed by a color correction processing unit according to the first embodiment of the disclosure.

FIG. 11 is a diagram illustrating sensitivity characteristics of the image $P_R$, the image $P_G$, and the image $P_B$ obtained by removing IR information (IR component) from each of the interpolation image $P_{R1}$, the interpolation image $P_G$ and the interpolation image $P_B$ by the color correction processing unit 33. In FIG. 11, the horizontal axis represents the wavelength (nm) and the vertical axis represents the sensitivity. In FIG. 11, a curve $L_{B1}$ illustrates a sensitivity characteristic when IR information (IR component) has been removed from each of the interpolation images $P_B$, and a curve $L_{G1}$ illustrates a sensitivity characteristic when IR information (IR component) has been removed from each of the interpolation images $P_G$, and a curve $L_{R3}$ illustrates a sensitivity characteristic when IR information (IR component) has been removed from each of the interpolation images $P_R$.

As illustrated by curves $L_{B1}$, $L_{G1}$ and $L_{R3}$ in FIG. 11, the color correction processing unit 33 performs color correction processing to obtain the sensitivity characteristics from which the wavelength band of infrared light has been removed from each of the pixel R1, the pixel G, and the pixel B. That is, the pixel R1, the pixel G, and the pixel B having pixel values after color correction by the color correction processing unit 33 correspond to pixel values obtained by capturing with the imaging apparatus having an infrared cutoff filter. Moreover, the pixel value of the pixel R2 is information having an infrared cutoff filter, and thus, the pixel R2 has data having high correlation with the pixel value of the pixel R1 after color correction. This makes it possible to perform highly accurate color correction processing by the color correction processing unit 33 toward the pixel R1. Furthermore, by calculating the correction coefficient using the pixel value (information) of the pixel R2 including the infrared cutoff filter provided on the light receiving surface and the pixel value (information) of the pixel IR, it is possible to perform color correction processing by the color correction processing unit 33 with high accuracy also toward the pixel value of each of the pixel G and the pixel B. As a result, it is possible to simultaneously capture the visible light image and the infrared light image while maintaining the resolution of the visible light image.

In a case in Step S204 where the color correction of all the pixels of the interpolation image generated by the interpolation image generation unit 32 is not finished (Step S204: No), the image processing apparatus 3 returns to the above-described Step S202.

According to the above-described first embodiment of the disclosure, at least a portion of the pixels R2 included in the second image sensor 22 is arranged at a position corresponding to the position of the pixel R1 included in the first image sensor 21 and at a position overlapping with the pixel R1 in the stacking direction, and at least a portion of the pixels IR included in the second image sensor 22 is arranged at a position corresponding to any of the positions of the pixel G and the pixel B included in the first image sensor 21 and at a position overlapping with any of the pixel G and the pixel B in the stacking direction. With this arrangement, it is possible to enhance the accuracy of the color correction processing while maintaining the resolution of the visible light image in simultaneously capturing the visible light image and the infrared light image.

Moreover, according to the first embodiment of the disclosure, the infrared cutoff filter to cut off the infrared light is provided (stacked) on the light receiving surface of the pixel R2. Accordingly, it possible to enhance accuracy in color correction performed by the color correction processing unit 33.

Moreover, according to the first embodiment of the disclosure, the information available for color correction by the color correction processing unit 33 increases to five colors, and both information with an infrared cutoff filter (filter R2) and without the infrared cutoff filter (filter R1) are available for a red color. Accordingly, it is possible to enhance accuracy of color correction and suppress deterioration of color reproducibility of the visible light image as compared with the usual color correction by three colors.

While the first embodiment of the disclosure is a case where the interpolation image generation unit 32 performs interpolation processing independently for each of the first image corresponding to the first image data generated by the upper-layer first image sensor 21 and the second image corresponding to the second image data generated by the lower-layer second image sensor 22, it is also allowable to generate interpolation images by performing the interpolation processing using the information included in mutual images. For example, in a case of interpolating the pixel R2 of the second image P22 generated by the lower-layer second image sensor 22, the interpolation image generation unit 32 may extract edge information from the interpolation image $P_{R1}$ of the pixel R1 of the first image P21 generated by the first image sensor 21 and may use the extracted edge information to perform interpolation processing of interpolating the pixels R2 of the second image P22 to generate the interpolation image $P_{R2}$. With this configuration, it is possible to improve the interpolation accuracy of the lower layer by using the information of the upper layer where highly accurate interpolation is performed.

Second Embodiment

Next, a second embodiment of the disclosure will be described. The second embodiment has a difference in the configuration of the lower-layer second image sensor of the multi-layer image sensor and in the processing executed by the image processing apparatus 3. In the following, the configuration of the lower-layer second image sensor in the multi-layer image sensor according to the second embodiment will be first described and thereafter the processing performed by the image processing apparatus according to the second embodiment will be described. A same reference sign will be given to the configuration identical to the configuration of the imaging system 1 according to the above-described first embodiment, and description for this will be omitted.

Configuration of Multi-layer Image Sensor

Figure 12:
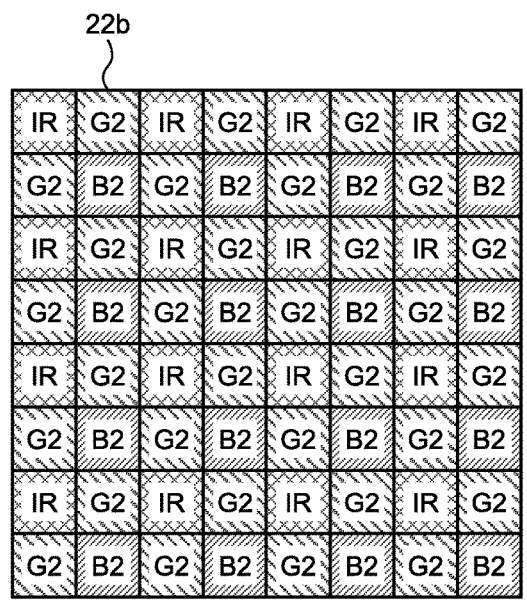
FIG. 12 is a diagram schematically illustrating a configuration of a lower-layer second image sensor in a multi-layer image sensor according to a second embodiment of the disclosure.

FIG. 12 is a diagram schematically illustrating a configuration of the lower-layer second image sensor in the multi-layer image sensor according to the second embodiment.

As illustrated in FIG. 12, a second image sensor 22b includes: the fifth pixel having sensitivity in the visible light band and having sensitivity of a predetermined value or more at a boundary between the visible light band and the infrared light band; and the third pixel having sensitivity in the infrared light band, the pixels being arranged in a two-dimensional matrix. Specifically, the second image sensor 22b uses a filter G2 having a maximum value of the transmission spectrum within the visible light band, a filter B2 having a maximum value of the transmission spectrum within the visible light band, and a filter IR having sensitivity in the infrared light band to form a predetermined array pattern. Each filter forming this array pattern is arranged at a position corresponding to any of the plurality of pixels. In the following, the pixel including each of the filter B2, the filter G2, and the filter IR provided on the light receiving surface will be expressed as a pixel B2, a pixel G2, and a pixel IR, respectively. Furthermore, the pixel B2 and the pixel G2 included in the second image sensor 22b are arranged at a portion corresponding to any of the positions of the pixel B (second pixel) and the pixel G (second pixel) included in the first image sensor 21 and at a position overlapping with any of the pixel B and the pixel G in the stacking direction. Furthermore, the pixel IR included in the second image sensor 22b is arranged at a position corresponding to the position of the pixel R1 (first pixel) included in the first image sensor 21 and at a position overlapping with the pixel G in the stacking direction.

Figure 13:
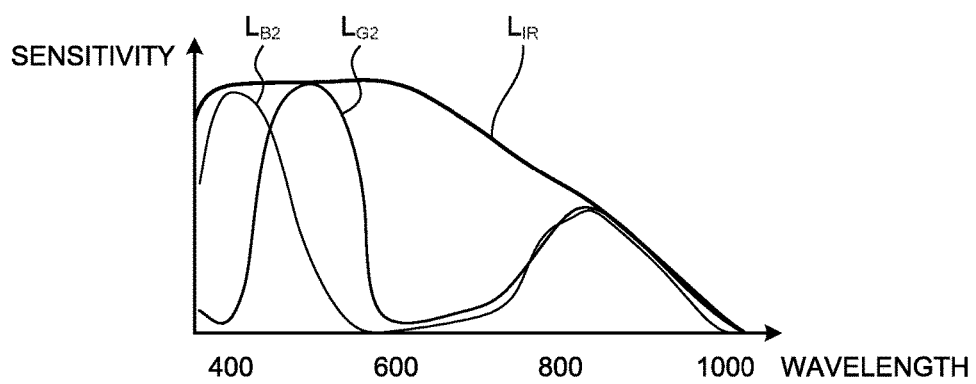
FIG. 13 is a diagram illustrating an exemplary sensitivity characteristic of each of pixels of the second image sensor according to the second embodiment of the disclosure.

FIG. 13 is a diagram illustrating an exemplary sensitivity characteristic of each of the pixels of the second image sensor 22b. In FIG. 13, the horizontal axis represents the wavelength (nm) and the vertical axis represents the sensitivity. In FIG. 13, a curve $L_{B2}$ illustrates a sensitivity characteristic of the pixel B2, a curve $L_{G2}$ illustrates a sensitivity characteristic of the pixel G2, and a curve $L_{IR}$ illustrates a sensitivity characteristic of the pixel IR.

As illustrated by the curve $L_{B2}$ in FIG. 13, the pixel B2 has a maximum value of sensitivity in the wavelength band of visible light of 400 nm to 550 nm and also has sensitivity to a portion of the light in the wavelength band of infrared light of 750 nm to 950 nm. As illustrated by the curve $L_{G2}$ in FIG. 13, the pixel G2 has a maximum value of sensitivity in the wavelength band of visible light of 495 nm to 570 nm and also has sensitivity to a portion of the light in the wavelength band of infrared light of 750 nm to 950 nm.

Figure 14:
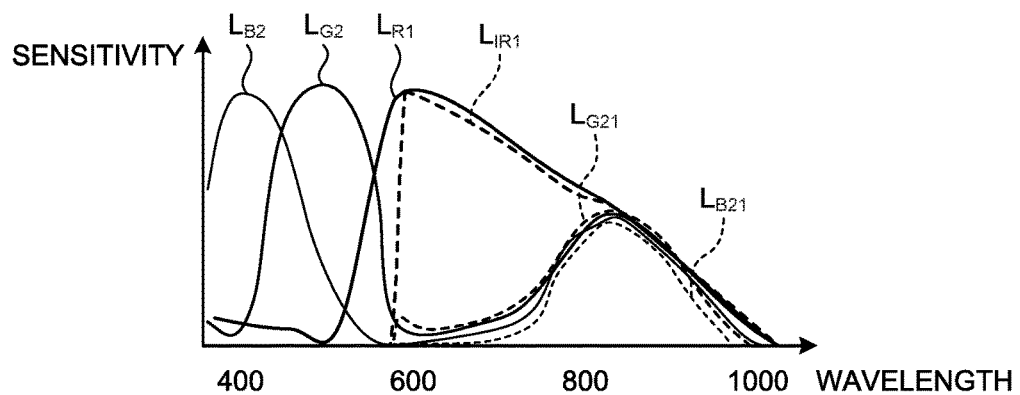
FIG. 14 is a diagram illustrating an exemplary sensitivity characteristic of each of pixels in a case where the first image sensor is stacked on the second image sensor according to the second embodiment of the disclosure.

FIG. 14 is a diagram illustrating an exemplary sensitivity characteristic of each of pixels in a case where the first image sensor 21 is stacked on the second image sensor 22b. In FIG. 14, the horizontal axis represents wavelength (nm) and the vertical axis represents sensitivity. In FIG. 14, the curve $L_{R1}$ illustrates a sensitivity characteristic of the pixel R1, the curve $L_{G2}$ illustrates a sensitivity characteristic of the pixel G2, the curve $L_{B2}$ illustrates a sensitivity characteristic of the pixel B2, a curve $L_{G21}$ illustrates a sensitivity characteristic of the pixel G2 in a case where the first image sensor 21 is stacked on the second image sensor 22b, a curve $L_{B21}$ illustrates a sensitivity characteristic of the pixel B2 in a case where the first image sensor 21 is stacked on the second image sensor 22b, and a curve $L_{IR1}$ illustrates a sensitivity characteristic of the pixel IR in a case where the first image sensor 21 is stacked on the second image sensor 22b.

As illustrated in FIG. 14, the light having a short wavelength is absorbed by the first image sensor 21, and thus, the second image sensor 22b cannot receive light having a short wavelength. Therefore, as illustrated by the curves $L_{G21}$, $L_{B21}$ and $L_{IR1}$, each of the pixel G2, pixel B2, and the pixel IR has no sensitivity to a wavelength of 600 nm or less.

Operation of Image Processing Apparatus

Figure 15:
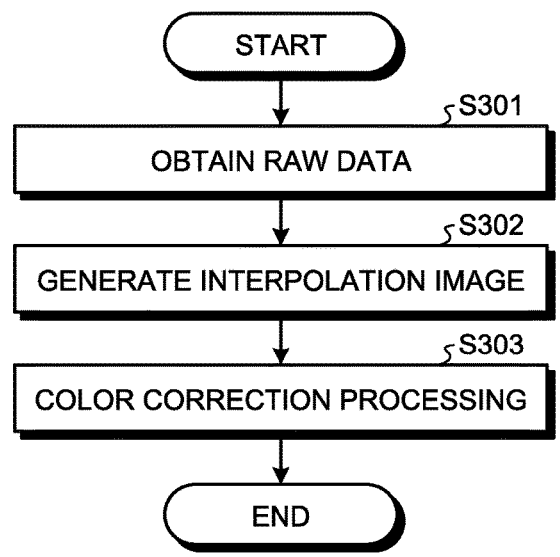
FIG. 15 is a flowchart illustrating outline of processing executed by an image processing apparatus according to the second embodiment of the disclosure.
Figure 16:
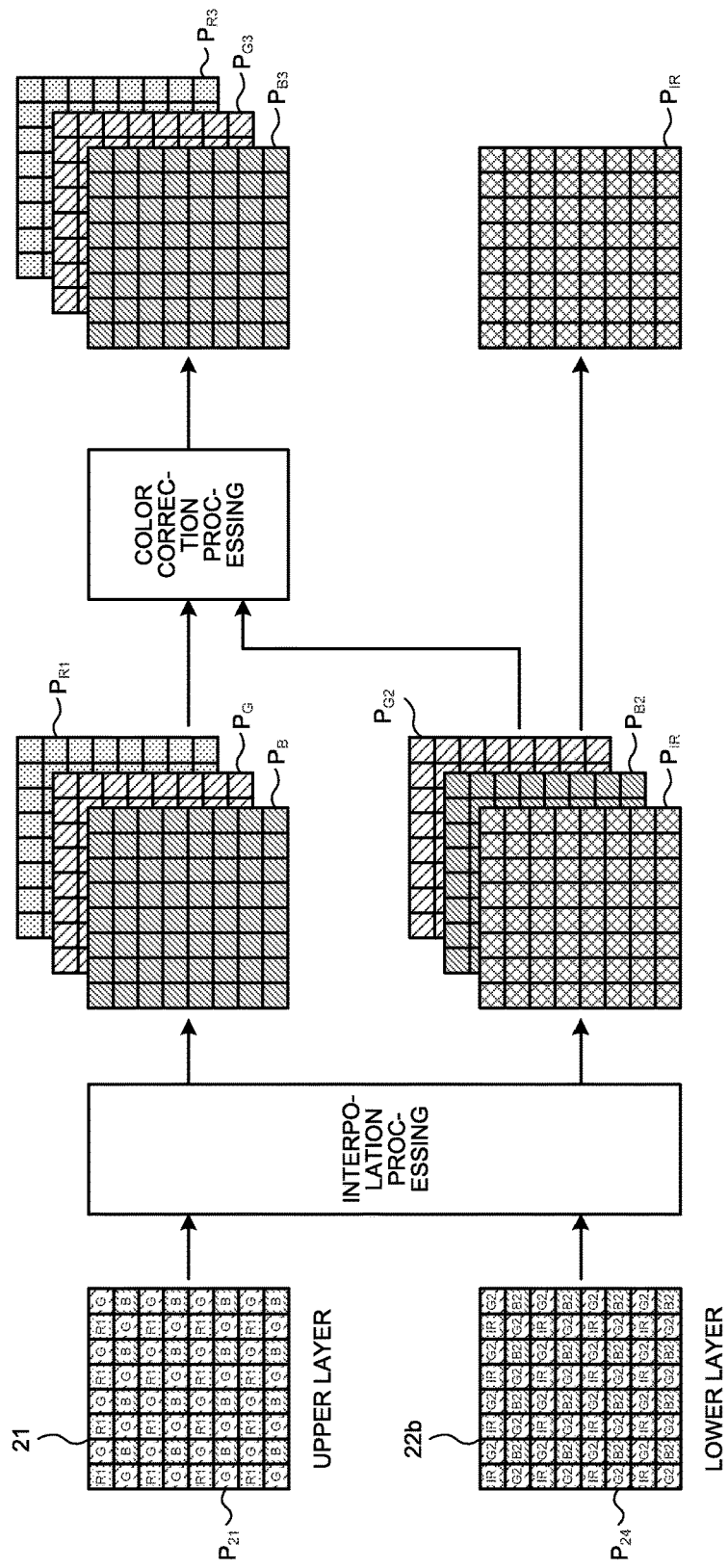
FIG. 16 is a schematic diagram illustrating outline of processing executed by the image processing apparatus according to the second embodiment of the disclosure.

Next, processing executed by the image processing apparatus 3 will be described. FIG. 15 is a flowchart illustrating an outline of processing executed by the image processing apparatus 3. FIG. 16 is a schematic diagram illustrating an outline of processing executed by the image processing apparatus 3 according to the second embodiment.

As illustrated in FIG. 15, the image acquisition unit 31 first obtains each of the first image data and the second image data as RAW data generated by the multi-layer image sensor 2 (Step S301). Specifically, as illustrated in FIG. 16, the image acquisition unit 31 obtains a first image P21 corresponding to the first image data generated by the upper-layer first image sensor 21 and a second image P24 generated by the lower-layer second image sensor 22b from the multi-layer image sensor 2.

Subsequently, the interpolation image generation unit 32 generates an interpolation image corresponding to the interpolation image data for each of the first image P21 and the second image P24 obtained by the image acquisition unit 31 (Step S302). Specifically, as illustrated in FIG. 16, the interpolation image generation unit 32 performs interpolation processing of interpolating each of the pixel R1, the pixel G, and the pixel B toward the first image P21 obtained by the image acquisition unit 31 to generate an interpolation image $P_{R1}$, an interpolation image $P_G$ and an interpolation image $P_B$ corresponding to the interpolation image data of each of the colors. Furthermore, the interpolation image generation unit 32 performs interpolation processing of interpolating each of the pixel B2, the pixel G2, and the pixel IR toward the second image P24 obtained by the image acquisition unit 31 to generate each of an interpolation image $P_{B2}$, an interpolation image $P_{G2}$, and an interpolation image $P_{IR}$ for each of the pixel B2, pixel G2, and the pixel IR, respectively.

Thereafter, the color correction processing unit 33 uses the interpolation images generated by the interpolation image generation unit 32 to perform color correction processing for each of the pixels (Step S303). Specifically, the color correction processing unit 33 first obtains a correction coefficient from the correction coefficient recording unit 341 and obtains a pixel value of the target pixel in the interpolation image generated by the interpolation image generation unit 32. Subsequently, the color correction processing unit 33 calculates the corrected pixel value using the obtained pixel value of the target pixel, the correction coefficient, and Formula (2).

$$\begin{bmatrix} R \\ G \\ B \end{bmatrix} = T_{3 \times 6} \begin{bmatrix} Ri \\ Gi \\ Bi \\ IR_G \\ IR_B \\ IR \end{bmatrix} \quad (2)$$

In Formula (2), each of R, G, and B represents a pixel value after color correction, T represents a correction coefficient, and each of Ri, Gi, and Bi represents a pixel value of an interpolation image obtained by interpolating the first image data generated by the first image sensor 21 including IR information, $IR_G$ represents a pixel value of an interpolation image $P_{G2}$ obtained by interpolating the second image data generated by the second image sensor 22b, $IR_B$ represents a pixel value of an interpolation image $P_{B2}$ obtained by interpolating the second image data generated by the second image sensor 22b, and IR represents a pixel value of the pixel IR.

Thereafter, in a case where the color correction of all the pixels of the interpolation image generated by the interpolation image generation unit 32 is finished, the image processing apparatus 3 ends the present processing. With this processing, as illustrated in FIG. 16, the color correction processing unit 33 generates each of the image $P_{R3}$, the image $P_{G3}$, and the image $P_{B3}$ obtained by removing IR information (IR component) from each of the interpolation image $P_{R1}$, the interpolation image $P_G$ and the interpolation image $P_B$, respectively.

Figure 17:
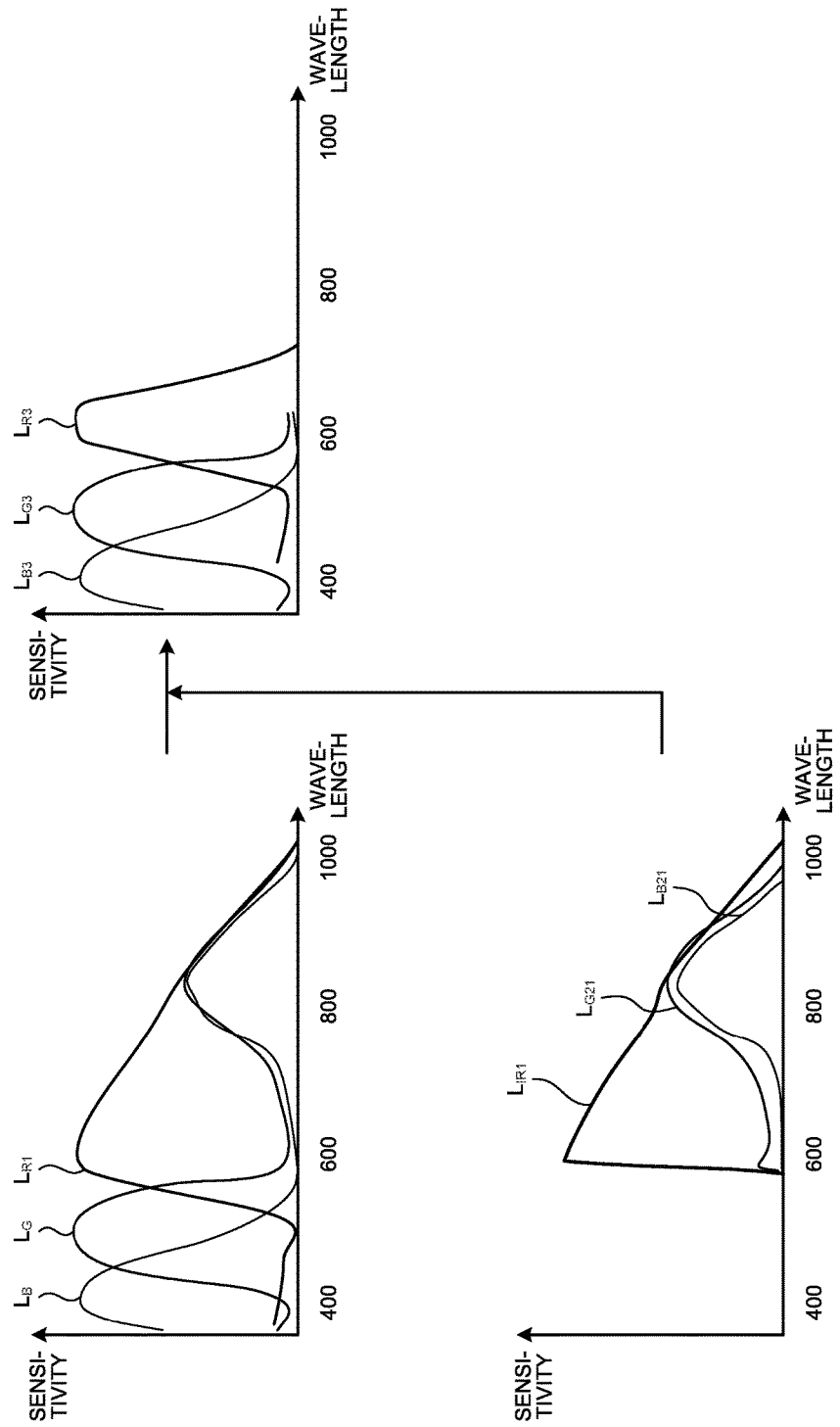
FIG. 17 is a schematic diagram illustrating outline of color correction executed by a color correction processing unit according to the second embodiment of the disclosure.

FIG. 17 is a diagram illustrating sensitivity characteristics of the image $P_R$, the image $P_G$, and the image $P_B$ obtained by removing IR information (IR component) from each of the interpolation image $P_{R1}$, the interpolation image $P_G$ and the interpolation image $P_B$ by the color correction processing unit 33. In FIG. 17, the horizontal axis represents wavelength (nm) and the vertical axis represents sensitivity. In FIG. 17, a curve $L_{B3}$ illustrates a sensitivity characteristic when IR information (IR component) has been removed from each of the interpolation images $P_B$, a curve $L_{G3}$ illustrates a sensitivity characteristic when IR information (IR component) has been removed from each of the interpolation images $P_G$, and a curve $L_{R3}$ illustrates a sensitivity characteristic when IR information (IR component) has been removed from each of the interpolation images $P_R$.

As illustrated by curves $L_{B3}$, $L_{G3}$ and $L_{R3}$ in FIG. 17, the color correction processing unit 33 performs color correction processing to obtain the sensitivity characteristics obtained by removing the wavelength band of infrared light from each of the pixel R1, the pixel G, and the pixel B. That is, information of the visible light and infrared light is obtained by the pixel B and the pixel G of the first image sensor 21 respectively for the blue and green colors and the infrared light information is selectively obtained by the lower-layer second image sensor 22b. The obtained information is used to calculate the correction coefficient to enable correction of the pixel values, particularly the values of the pixels B and C by highly accurate color correction processing. As a result, it is possible to simultaneously capture the visible light image and the infrared light image while maintaining the resolution of the visible light image.

According to the above-described second embodiment of the disclosure, at least a portion of the pixels G2 and the pixels B2 included in the second image sensor 22b is arranged at a position corresponding to any of the positions of the pixels B and the pixels G included in the first image sensor 21 and at a position overlapping with any of the pixel B and the pixel G in the stacking direction, and at least a portion of the pixels IR included in the second image sensor 22b is arranged at a position corresponding to the position of the pixel R1 included in the first image sensor 21 and at a position overlapping with the pixel R1 in the stacking direction. With this arrangement, it is possible to enhance the accuracy of the color correction processing while maintaining the resolution of the visible light image in simultaneously capturing the visible light image and the infrared light image.

While the second embodiment of the disclosure is a case where the interpolation image generation unit 32 performs interpolation processing independently for each of the first image corresponding to the first image data generated by the upper-layer first image sensor 21 and the second image corresponding to the second image data generated by the lower-layer second image sensor 22b, it is also allowable to generate interpolation images by performing the interpolation processing using the information included in mutual images. For example, in the case of interpolating a pixel value of each of the pixels of the first image P21 generated by the first image sensor 21, the interpolation image generation unit 32 may extract edge information from the interpolation image $P_{R2}$ of the second image P22 generated by the lower-layer second image sensor 22b and may use the extracted edge information to perform interpolation processing toward the first image P21 generated by the first image sensor 21. With this configuration, it is possible to enhance the accuracy of the interpolation processing of the first image P21 generated by the first image sensor 21 in shooting a subject having a high correlation between visible light and infrared light, or in shooting under a light source.

Third Embodiment

Next, a third embodiment of the disclosure will be described. In the third embodiment, an optical filter that does not transmit light of a predetermined wavelength band is arranged between an optical system (not illustrated) and the multi-layer image sensor. A same reference sign will be given to the configuration identical to the configuration of the imaging system 1 according to the above-described first embodiment, and description for this will be omitted.

Configuration of Imaging System

Figure 18:
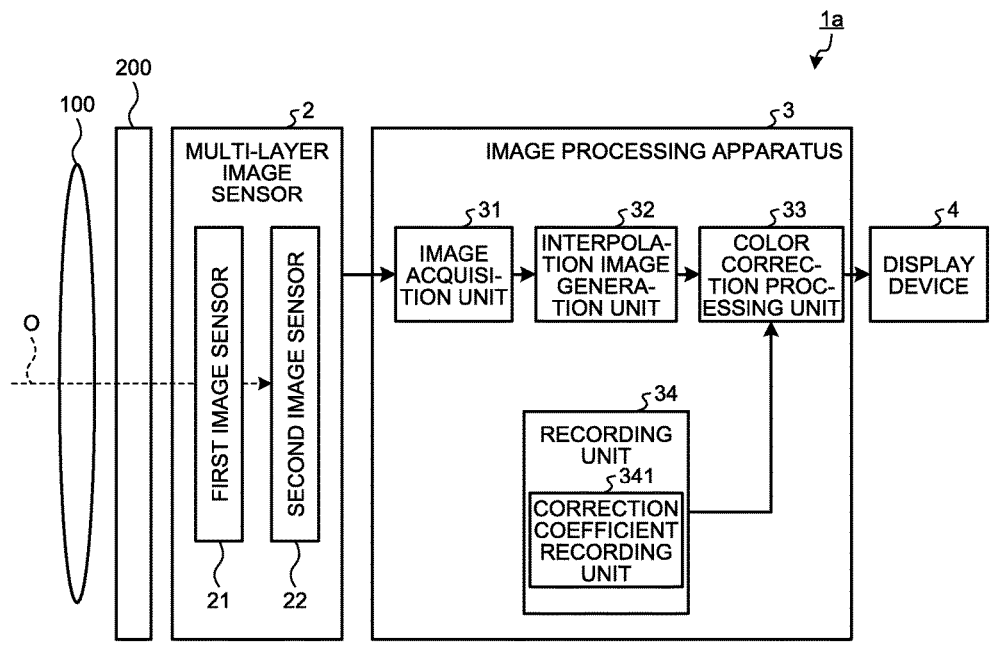
FIG. 18 is a block diagram illustrating a functional configuration of an imaging system according to a third embodiment of the disclosure.

FIG. 18 is a block diagram illustrating a functional configuration of an imaging system according to the third embodiment of the disclosure. An imaging system 1a illustrated in FIG. 18 further includes an optical filter 200 in addition to the configuration of the imaging system 1 according to the above-described first embodiment.

The optical filter 200 is arranged between the optical system 100 and the multi-layer image sensor 2. The optical filter 200 includes a notch filter that does not transmit light of a predetermined wavelength band.

Figure 19:
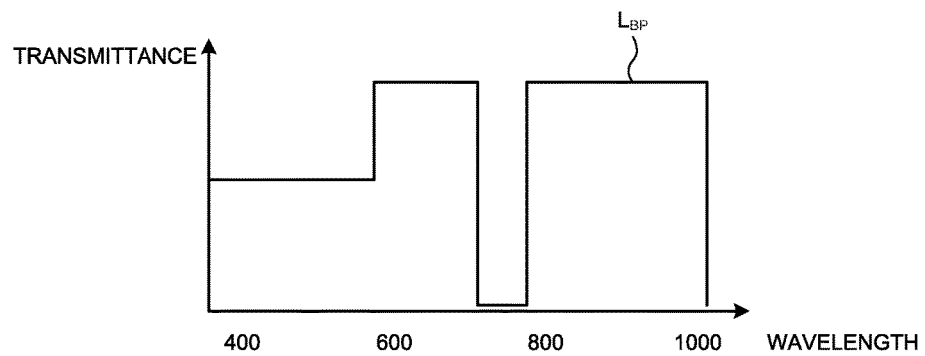
FIG. 19 is a diagram illustrating an exemplary transmission characteristic of an optical filter according to the third embodiment of the disclosure.

FIG. 19 is a diagram schematically illustrating an exemplary transmission characteristic of the optical filter 200. In FIG. 19, the horizontal axis represents wavelength (nm) and the vertical axis represents transmittance. Moreover, a broken line $L_{BP}$ in FIG. 19 indicates a transmission characteristic of the optical filter 200.

As illustrated by the broken line $L_{BP}$ in FIG. 19, the optical filter 200 has a transmission characteristic of not transmitting the light in the neighborhood of the wavelength band of 750 nm to 800 nm. As a result, the optical filter 200 does not transmit the light in the neighborhood of the wavelength band of 750 nm to 800 nm in a case where the image processing apparatus 3 performs color correction processing. Accordingly, it is possible to perform color correction processing of each of pixels with high accuracy. The optical filter 200 is particularly effective when shooting a fluorescent component. Since a typical fluorescent component is light of low levels in many cases, application of strong excitation light is often used as a method for shooting the fluorescent component. The optical filter 200 cuts off the wavelength band of the excitation light emitted onto the subject in fluorescence observation. The case illustrated in FIG. 19 would be effective in emission of the excitation light in the neighborhood of the wavelength band of 750 nm to 800 nm by a light source device (not illustrated) to capture the fluorescence in the infrared light band of 800 nm or above.

According to the above-described third embodiment of the disclosure, the optical filter 200 that does not transmit the light in the neighborhood of the wavelength band of 750 nm to 800 nm is provided between the optical system (not illustrated) and the multi-layer image sensor 2. With this configuration, the image processing apparatus 3 can perform color correction processing of each of pixels with high accuracy.

Furthermore, according to the third embodiment of the disclosure, the optical filter 200 is provided to cut off information of the wavelength band that need not be obtained in the wavelength band of infrared light. Accordingly, it is possible to perform color correction processing with high accuracy.

While the third embodiment of the disclosure arranges the optical filter 200 between the optical system 100 and the multi-layer image sensor 2, the optical filter 200 may be arranged on the front side (subject side) of the optical system 100, for example. Specifically, it is allowable to arrange the optical filter 200, the optical system 100, and the multi-layer imaging sensor 2 in this order along the optical axis O. In a case of using a camera system such as a single lens reflex camera including a main body integrally formed with the multi-layer image sensor 2, the image processing apparatus 3 and the display device 4 and including a lens apparatus including the optical system 100 and detachable from the main body, the optical filter 200 may of course be configured to be detachable from the lens apparatus.

First Modification

Figure 20:
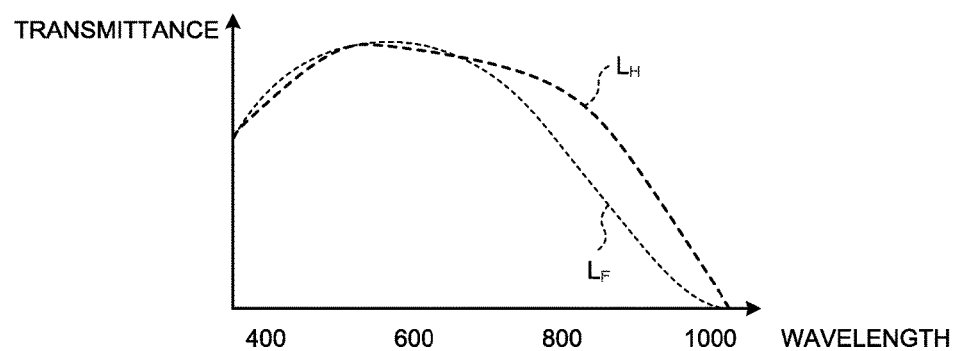
FIG. 20 is a diagram schematically illustrating spectral characteristics of a first image sensor and a second image sensor according to a first modification of the embodiment of the disclosure.

In the embodiment of the disclosure, the spectral characteristics of the first image sensor and the second image sensor can be made mutually different. FIG. 20 is a diagram schematically illustrating spectral characteristics of a first image sensor and a second image sensor according to a first modification of the embodiment of the disclosure. In FIG. 20, the horizontal axis represents wavelength and the vertical axis represents transmittance. Moreover, in FIG. 20, a curve $L_H$ represents a spectral characteristic of the upper-layer first image sensor, and a curve $L_F$ represents a spectral characteristic of the lower-layer second image sensor.

As illustrated in FIG. 20, the multi-layer image sensor may be formed using a substrate in which the spectral characteristics of the upper-layer first image sensor and the lower-layer second image sensor are mutually different.

The above-described first modification of the embodiment of the disclosure uses a substrate in which the spectral characteristics of the upper-layer first image sensor and the lower-layer second image sensor are mutually different, making it possible to transmit the light of a desired wavelength band.

Second Modification

Figure 21:
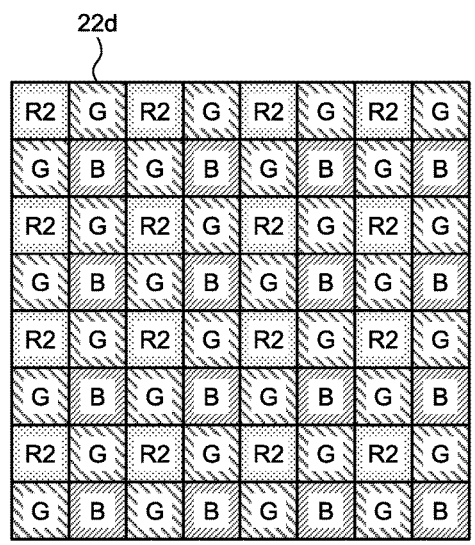
FIG. 21 is a diagram schematically illustrating a configuration of a second image sensor according to a second modification of the embodiment of the disclosure.

In the embodiment of the disclosure, it is possible to further change the configuration of the second image sensor. FIG. 21 is a diagram schematically illustrating a configuration of a second image sensor according to a second modification of the embodiment of the disclosure.

A second image sensor 22d illustrated in FIG. 21 uses a filter R2 having a maximum value of the transmission spectrum within the visible light band and filters G and B having mutually different maximum values of the transmission spectrum within the visible light band to form a predetermined array pattern (Bayer pattern). Each color filter forming this array pattern is arranged at a position corresponding to any of the plurality of pixels. In this case, each of the pixel B and the pixel G in the second image sensor 22d can receive the light in the wavelength band of infrared light.

According to the above-described second modification of the embodiment of the disclosure, it is possible to enhance the accuracy of the color correction processing performed by the image processing apparatus 3.

Third Modification

In the embodiment of the disclosure, it is possible to further change the configuration of the first image sensor.

Figures 22, 23:
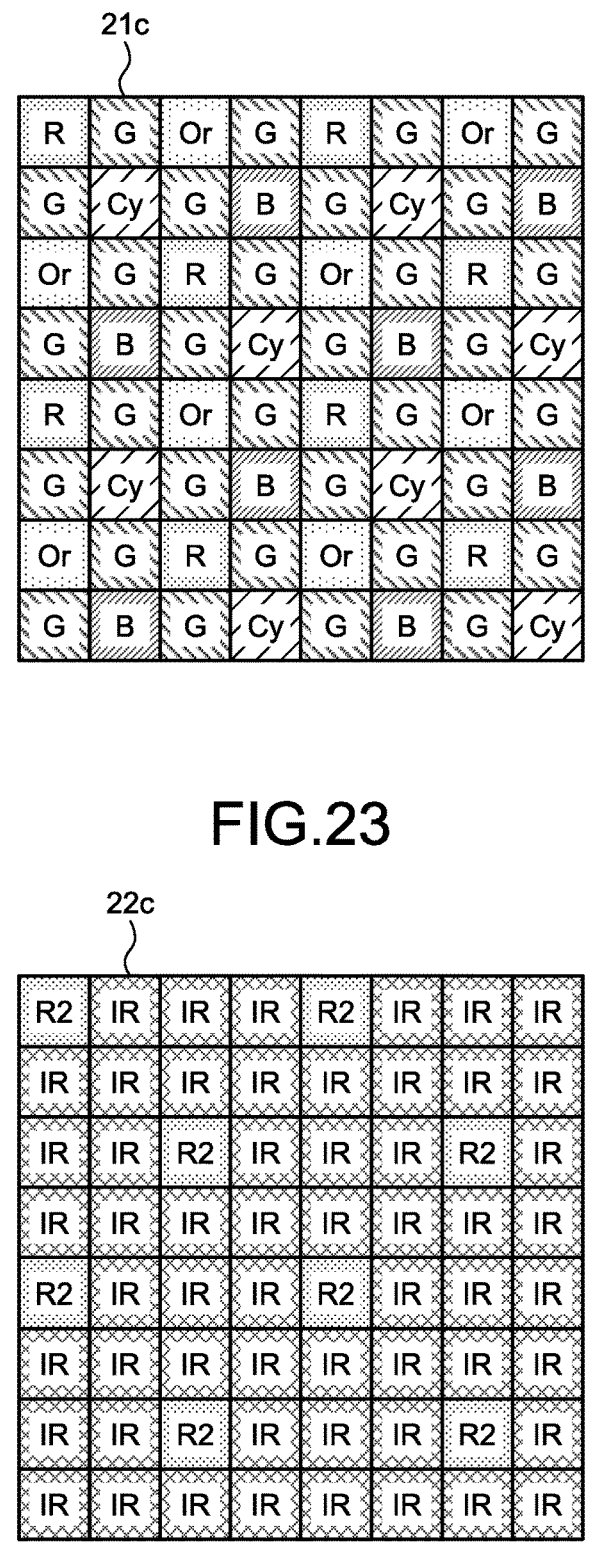

FIG. 22 is a diagram schematically illustrating a configuration of a first image sensor according to a third modification of the embodiment of the disclosure.

A first image sensor 21c illustrated in FIG. 22 uses filters R and G having mutually different maximum values of the transmission spectrum within the visible light band and uses a complementary color filter Cy (cyan) and a complementary color filter Or (orange) having maximum values of the transmission spectrum within the visible light band to form a predetermined array pattern. Each filter forming this array pattern is arranged at a position corresponding to any of the plurality of pixels.

FIG. 23 is a diagram schematically illustrating a configuration of the second image sensor according to the third modification of the embodiment of the disclosure.

A second image sensor 22c illustrated in FIG. 23 uses a filter R2 having a maximum value of the transmission spectrum within the wavelength band of visible light and a filter IR that transmits light in the wavelength band of visible light and the wavelength band of infrared light to form a predetermined array pattern. Each filter forming this array pattern is arranged at a position corresponding to any of the plurality of pixels.

With the above-described third modification of the embodiment of the disclosure, there are provided effects similar to the effects of the above-described first to third embodiments.

Fourth Modification

Figure 24:
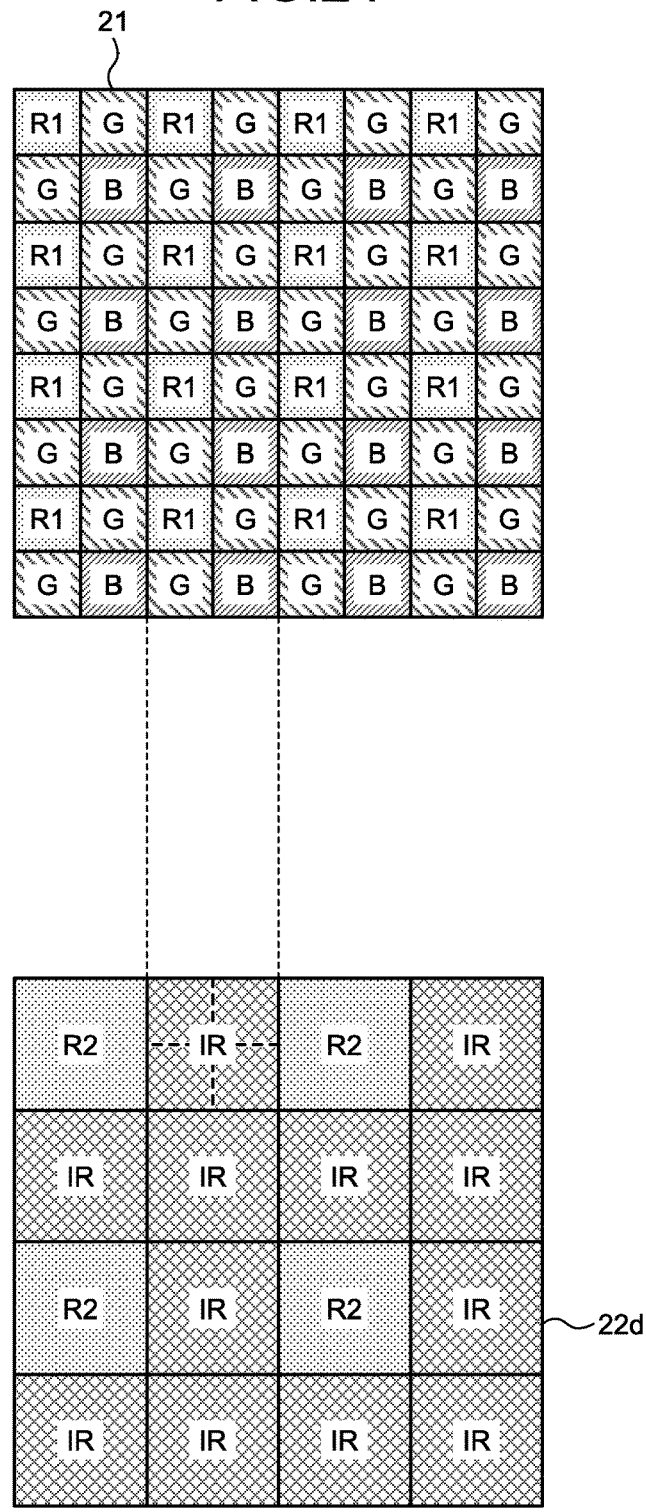
FIG. 24 is a diagram schematically illustrating configurations of a first image sensor and a second image sensor according to a fourth modification of the embodiment of the disclosure.

In the embodiment of the disclosure, the area of each of pixels of the first image sensor and each of pixels of the second image sensor can be made different. FIG. 24 is a diagram schematically illustrating configurations of the first image sensor and the second image sensor according to a fourth modification of the embodiment of the disclosure.

As illustrated in FIG. 24, a second image sensor 22d uses a filter R2 having a maximum value of the transmission spectrum within the wavelength band of visible light and a filter IR that transmits light in the wavelength band of visible light and the wavelength band of infrared light to form a predetermined array pattern. Each filter forming this array pattern is arranged at a position corresponding to any of the plurality of pixels. Furthermore, by making the area of each of the pixels R2 and the pixels IR included in the second image sensor 22d larger than the area of each of the pixels R1, G and B included in the first image sensor 21, resolution of the first image sensor 21 and the resolution of the second image sensor 22d are made mutually different. Specifically, by making the pixel area of the pixel R2 and the pixel IR four times the area of each of the pixel R1, the pixel G, and the pixel B, the amount of light incident per pixel is increased, making it possible to compensate for the insufficient sensitivity of the second image sensor 22d.

According to the above-described fourth modification of the embodiment of the disclosure, each of the pixels R2 and the pixels IR included in the second image sensor 22d is made larger than the area of each of the pixels R, G pixels and B pixels included in the first image sensor 21 to increase the amount of light incident per pixel in the second image sensor 22d, making it possible to compensate for the insufficient sensitivity of the second image sensor 22d.

Fifth Modification

Figure 25:
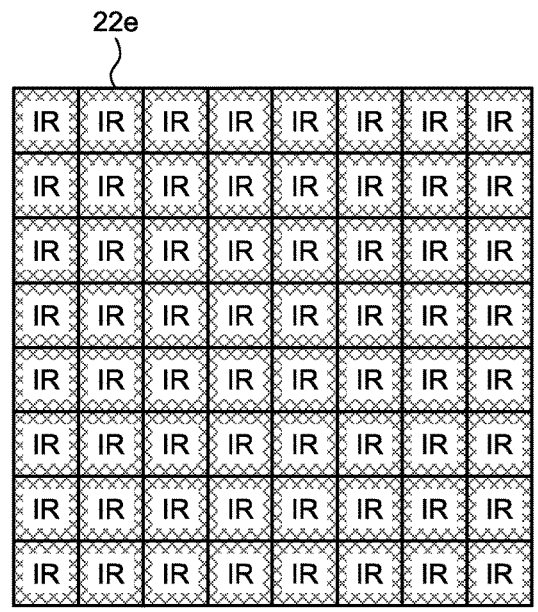
FIG. 25 is a diagram schematically illustrating a configuration of a second image sensor according to a fifth modification of the embodiment of the disclosure.

In the present embodiment, an infrared filter can also be used. FIG. 25 is a diagram schematically illustrating a configuration of a second image sensor according to a fifth modification of the embodiment of the disclosure.

Figure 26:
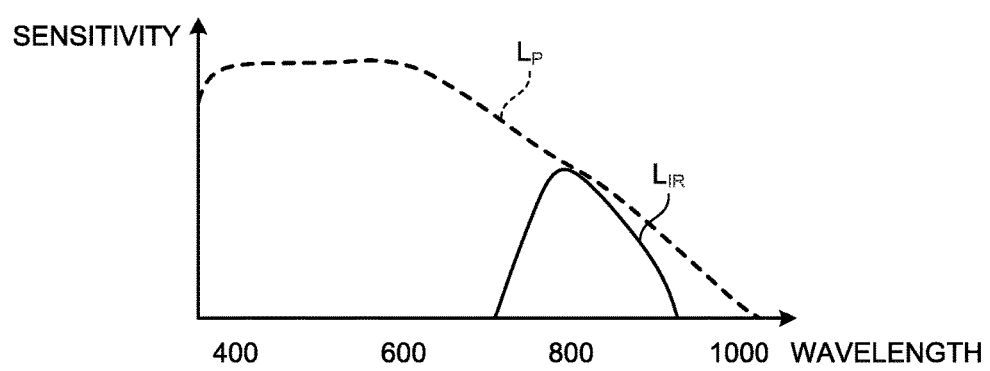
FIG. 26 is a diagram illustrating an exemplary sensitivity characteristic of a pixel IR of the second image sensor according to the fifth modification of the embodiment of the disclosure.

As illustrated in FIG. 25, a second image sensor 22e uses a filter IR that transmits light in the wavelength band of the infrared light to form a predetermined array pattern. Each filter forming this array pattern is arranged at a position corresponding to any of the plurality of pixels. p FIG. 26 is a diagram illustrating an exemplary sensitivity characteristic of the pixel IR of the second image sensor 22e. In FIG. 26, the horizontal axis represents wavelength (nm) and the vertical axis represents sensitivity. In FIG. 26, a curve $L_P$ represents a sensitivity characteristic of the pixel with a filter not being arranged, and a curve $L_{IR}$ represents a sensitivity characteristic of the pixel IR.

As illustrated by the curve $L_{IR}$ in FIG. 26, the second image sensor 22e may have sensitivity in a specific wavelength band of infrared light alone. As a result, it is possible to obtain information of the specific wavelength band in the infrared light.

According to the above-described fifth modification of the embodiment of the disclosure, the second image sensor 22e includes solely the filters IR to transmit the light in the specific wavelength band of the infrared light on each of pixels, making it possible to obtain information on the specific wavelength band of the infrared light.

Sixth Modification

While the color correction processing unit 33 performs color correction processing with the RGB space in the embodiments of the disclosure, color correction processing may be performed in the YCbCr space. For example, in the above-described first embodiment, the color correction processing unit 33 may first convert R, G, and B interpolation images corresponding to the first image data generated by the upper-layer first image sensor into the YCbCr space, and then may perform color conversion processing using Formula (3). This makes it possible to genuinely perform color information conversion while suppressing fluctuation of a luminance component (Y component).

$$\begin{bmatrix} R \\ G \\ B \end{bmatrix} = T_{3\times 5} \begin{bmatrix} Y \\ Cb \\ Cr \\ R_L \\ IR \end{bmatrix} \quad (3)$$

Other Embodiments

In the present embodiment, the first image sensor and the second image sensor need not have the same characteristic. For example, it is allowable to form the upper-layer first image sensor by a back-illumination sensor and to form the lower-layer second image sensor by a surface-illumination sensor. Alternatively, the upper-layer first image sensor may be formed by a surface-illumination sensor and the lower-layer second image sensor may be formed by a back-illumination sensor, and it is further possible to appropriately combine the surface-illumination sensor and the back-illumination sensor.

While the disclosure uses information on all colors (pixel values) generated by the multi-layer image sensor in the color correction processing, there is no need to use the all color information for color correction processing. For example, the color combination used for the color correction processing may differ depending on the type of the light source used at the time of shooting or the type of the subject to be shot, and it is sufficient to obtain the most suitable color combination at the time of calculating correction coefficients (calibration processing) in advance. In addition, the number of dimensions of the correction coefficient is not limited to the number exemplified in the above-described embodiment. Color correction processing may be performed using a higher dimensional correction coefficient, and existing or well-known color correction processing can be applied.

While the disclosure uses the primary color filter as a color filter, it is also allowable to use complementary color filters (Cy (cyan), Mg (magenta), and Ye (yellow)) transmitting light having complementary wavelength components. It is further allowable to use the color filters (R, G, B, Or, and Cy) combining the primary color filters and filters (Or and Cy) transmitting light having wavelength components of orange and cyan. Furthermore, it is allowable to use the color filters (R, G, B, and W) combining the primary color filters and a filter (W) transmitting light having a wavelength component of white.

Moreover, while the disclosure describes the image processing apparatus as an imaging system, the apparatus is also applicable to a processor used in an endoscope system or to an image processing unit of a capsule endoscope insertable into the body cavity of a subject. The image processing apparatus can of course be applied as an image engine of an imaging apparatus. Furthermore, the image processing apparatus may be incorporated in a processing apparatus used in a microscope system, or the like.

Moreover, in the description of the flowcharts for the operations described above in the present specification, terms such as "first", "next", "subsequently", and "thereafter" are used to describe operation for convenience. These do not denote, however, that the operations need to be performed in this order.

Moreover, the methods of the processing performed by the image processing apparatus in the above-described embodiments, that is, any of the processing illustrated in the flowcharts may be stored as a program that can be executed by a control unit such as a CPU. In addition, it is possible to distribute by storing in a storage medium of the external storage device, such as memory cards (ROM card, RAM card, etc.), a magnetic disk (floppy disk (registered trademark), hard disk, etc.), an optical disc (CD-ROM, DVD, etc.), or a semiconductor memory. The control unit such as a CPU reads the program stored in the storage medium of the external storage device and controls the operation by the read program to execute the above-described processing.

Moreover, note that the disclosure is not limited to the above-described embodiments and modifications just as they are but can be embodied by modifying the components without departing from the scope of the invention at a stage of implementation of the disclosure. Furthermore, a plurality of components disclosed in the above-described embodiments may be appropriately combined to form various inventions. For example, some components may be omitted from the all the components described in the embodiments and the modifications. Furthermore, the components described in each of the embodiments and modifications may be appropriately combined with each other.

Moreover, a term which has been described at least once in the specification or the drawings, associated with another term having a broader or similar meaning, may be substituted by this other term anywhere in the specification and the drawings. In this manner, various modifications and applications may be implemented within a scope that does not depart from the disclosure.

According to some embodiments, it is possible to enhance the accuracy of color correction processing while maintaining the resolution of the visible light image in simultaneously capturing the visible light image and the infrared light image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multi-layer image sensor comprising:
   a first image sensor including:
      a first pixel having sensitivity in a visible light band and having sensitivity of a first predetermined value or more at a boundary between the visible light band and an infrared light band; and
      a second pixel having sensitivity in the visible light band and having sensitivity less than the first predetermined value at the boundary between the visible light band and the infrared light band, the first and second pixels being arranged in a two-dimensional matrix, the first image sensor being configured to receive light and perform photoelectric conversion to generate first image data; and
   a second image sensor including:
      a third pixel having sensitivity in an infrared light band; and
      at least one of a fourth pixel and a fifth pixel, the fourth pixel having sensitivity in a visible light band and having sensitivity of a second predetermined value or more at a boundary between the visible light band and an infrared light band, the fifth pixel having sensitivity in the visible light band and having sensitivity less than the second predetermined value at the boundary between the visible light band and the infrared light band, the third pixel and the at least one of the fourth pixel and the fifth pixel being arranged in a two-dimensional matrix, the second image sensor being configured to receive light and perform photoelectric conversion to generate second image data, wherein
   the second image sensor has a light receiving surface where the first image sensor is stacked,
   at least a portion of the fourth pixel included in the second image sensor is arranged at a position corresponding to a position of the first pixel included in the first image sensor and at a position overlapping with the first pixel in a stacking direction of the first sensor, and
   at least a portion of the third pixel included in the second image sensor is arranged at a position corresponding to a position of the second pixel included in the first image sensor and at a position overlapping with the second pixel in the stacking direction of the first sensor.

2. The multi-layer image sensor according to claim 1, wherein the second image sensor includes an infrared cutoff filter to cut off the infrared light, the infrared cutoff filter being provided on a light receiving surface of the fourth pixel.

3. The multi-layer image sensor according to claim 2, wherein
   the first image sensor includes two types of second pixels each having a maximum value of sensitivity in mutually different visible light bands, with the number of one type of the second pixels being greater than other one type of the second pixels,
   the second image sensor includes the fourth pixel and the fifth pixel,
   at least a portion of the third pixel is arranged at a position corresponding to a position where the one type of the second pixels is arranged in the first image sensor and at a position overlapping with the one type of the second pixels in the stacking direction of the first sensor,
   at least a portion of the fifth pixel included in the second image sensor is arranged at a position corresponding to the one type of the second pixels in the first image sensor and at a position overlapping with the one type of the second pixels in the stacking direction of the first sensor, the at least the portion of the fifth pixel included in the second image sensor being arranged at a position where the third pixel is not arranged.

4. The multi-layer image sensor according to claim 1, wherein the second image sensor includes two types of second pixels each having a maximum value of sensitivity in mutually different visible light bands.

5. The multi-layer image sensor according to claim 1, wherein
   each of the first pixel and the fourth pixel has a maximum value of sensitivity in a wavelength band of a red color, and
   each of the second pixel and the fifth pixel has a maximum value of sensitivity in one of a wavelength band of a green color and a wavelength band of a blue color.

6. The multi-layer image sensor according to claim 1, wherein the first image sensor includes an optical filter to cut off light of a predetermined wavelength band, the optical filter being provided on a light receiving surface of the first image sensor.

7. An image processing apparatus comprising:
   an acquisition unit configured to obtain each of the first image data and the second image data generated by the multi-layer image sensor according to claim 1;
   an interpolation image generation unit configured to:
      generate a first interpolation image interpolating the first pixel of the first image sensor and a second interpolation image interpolating the second pixel of the first image sensor, based on the first image data obtained by the acquisition unit; and
      generate a third interpolation image interpolating the at least one of the fourth pixel and the fifth pixel of the second image sensor and a fourth interpolation image interpolating the third pixel of the second image sensor, based on the second image data obtained by the acquisition unit; and
   a color correction processing unit configured to perform color correction of the first interpolation image and the second interpolation image, based on the third interpolation image and the fourth interpolation image generated by the interpolation image generation unit.

8. The image processing apparatus according to claim 7, wherein the color correction processing unit is configured to perform color correction of the first interpolation image and the second interpolation image, based on the first interpolation image, the second interpolation image, the third interpolation image, and the fourth interpolation image.

9. The image processing apparatus according to claim 8, wherein the color correction processing unit is configured to perform color correction of the first interpolation image and the second interpolation image by using a value obtained by converting a pixel value of each of the first interpolation image, the second interpolation image, the third interpolation image, and the fourth interpolation image from a RGB color space into a YCbCr space.

10. The image processing apparatus according to claim 7, wherein
the interpolation image generation unit is configured to:
extract edge information included in at least one of the first interpolation image and the second interpolation image; and
generate at least one of the third interpolation image and the fourth interpolation image, based on the extracted edge information.

11. The image processing apparatus according to claim 7, wherein
the interpolation image generation unit is configured to:
extract edge information included in at least one of the third interpolation image and the fourth interpolation image; and
generate at least one of the first interpolation image and the second interpolation image, based on the extracted edge information.

12. An image processing method comprising:
obtaining each of the first image data and the second image data generated by the multi-layer image sensor according to claim 1;
generating a first interpolation image interpolating the first pixel of the first image sensor and a second interpolation image interpolating the second pixel of the first image sensor, based on the obtained first image data;
generating a third interpolation image interpolating the at least one of the fourth pixel and the fifth pixel of the second image sensor and a fourth interpolation image interpolating the third pixel of the second image sensor, based on the obtained second image data; and
performing color correction of the first interpolation image and the second interpolation image, based on the generated third interpolation image and the generated fourth interpolation image.

13. A non-transitory computer-readable recording medium with an executable program stored thereon, the program causing an image processing apparatus to execute:
obtaining each of the first image data and the second image data generated by the multi-layer image sensor according to claim 1;
generating a first interpolation image interpolating the first pixel of the first image sensor and a second interpolation image interpolating the second pixel of the first image sensor, based on the obtained first image data;
generating a third interpolation image interpolating the at least one of the fourth pixel and the fifth pixel of the second image sensor and a fourth interpolation image interpolating the third pixel of the second image sensor, based on the obtained second image data; and
performing color correction of the first interpolation image and the second interpolation image, based on the generated third interpolation image and the generated fourth interpolation image.

14. A multi-layer image sensor comprising:
a first image sensor including:
a first pixel having sensitivity in a visible light band and having sensitivity of a predetermined value or more at a boundary between the visible light band and an infrared light band; and
a second pixel having sensitivity in the visible light band and having sensitivity less than the predetermined value at the boundary between the visible light band and the infrared light band, the first and second pixels being arranged in a two-dimensional matrix, the first image sensor being configured to receive light and perform photoelectric conversion to generate first image data; and
a second image sensor including:
a third pixel having sensitivity in a infrared light band; and
at least one of the fourth pixel and the fifth pixel, the fourth pixel having sensitivity in a visible light band and having sensitivity of a second predetermined value or more at a boundary between the visible light band and an infrared light band, the fifth pixel having sensitivity in the visible light band and having sensitivity less than the second predetermined value at the boundary between the visible light band and the infrared light band, the third pixel and the at least one of the fourth pixel and the fifth pixel being arranged in a two-dimensional matrix, the second image sensor being configured to receive light and perform photoelectric conversion to generate second image data, wherein
the second image sensor has a light receiving surface where the first image sensor is stacked,
at least a portion of the fifth pixel included in the second image sensor is arranged at a position corresponding to a position of the second pixel included in the first image sensor and at a position overlapping with the second pixel in a stacking direction of the first sensor, and
at least a portion of the third pixel included in the second image sensor is arranged at a position corresponding to a position of the first pixel included in the first image sensor and at a position overlapping with the first pixel in the stacking direction of the first sensor.

15. The multi-layer image sensor according to claim 14, wherein
each of the first pixel and the fourth pixel has a maximum value of sensitivity in a wavelength band of a red color, and
each of the second pixel and the fifth pixel has a maximum value of sensitivity in one of a wavelength band of a green color and a wavelength band of a blue color.

16. The multi-layer image sensor according to claim 14, wherein the first image sensor includes an optical filter to cut off light of a predetermined wavelength band, the optical filter being provided on a light receiving surface of the first image sensor.

17. An image processing apparatus comprising:
an acquisition unit configured to obtain each of the first image data and the second image data generated by the multi-layer image sensor according to claim 14;
an interpolation image generation unit configured to:
generate a first interpolation image interpolating the first pixel of the first image sensor and a second interpolation image interpolating the second pixel of the first image sensor, based on the first image data obtained by the acquisition unit; and
generate a third interpolation image interpolating the at least one of the fourth pixel and the fifth pixel of the second image sensor and a fourth interpolation image interpolating the third pixel of the second image sensor, based on the second image data obtained by the acquisition unit; and a color correction processing unit configured to perform color correction of the first interpolation image and the second interpolation image, based on the third interpolation image and the fourth interpolation image generated by the interpolation image generation unit.

18. The image processing apparatus according to claim 17, wherein the color correction processing unit is configured to perform color correction of the first interpolation image and the second interpolation image, based on the first interpolation image, the second interpolation image, the third interpolation image, and the fourth interpolation image.

19. The image processing apparatus according to claim 18, wherein the color correction processing unit is configured to perform color correction of the first interpolation image and the second interpolation image by using a value obtained by converting a pixel value of each of the first interpolation image, the second interpolation image, the third interpolation image, and the fourth interpolation image from a RGB color space into a YCbCr space.

20. The image processing apparatus according to claim 17, wherein
the interpolation image generation unit is configured to:
extract edge information included in at least one of the first interpolation image and the second interpolation image; and
generate at least one of the third interpolation image and the fourth interpolation image, based on the extracted edge information.

21. The image processing apparatus according to claim 17, wherein
the interpolation image generation unit is configured to:
extract edge information included in at least one of the third interpolation image and the fourth interpolation image; and
generate at least one of the first interpolation image and the second interpolation image, based on the extracted edge information.

22. An image processing method comprising:
obtaining each of the first image data and the second image data generated by the multi-layer image sensor according to claim 14;
generating a first interpolation image interpolating the first pixel of the first image sensor and a second interpolation image interpolating the second pixel of the first image sensor, based on the obtained first image data;
generating a third interpolation image interpolating the at least one of the fourth pixel and the fifth pixel of the second image sensor and a fourth interpolation image interpolating the third pixel of the second image sensor, based on the obtained second image data; and
performing color correction of the first interpolation image and the second interpolation image, based on the generated third interpolation image and the generated fourth interpolation image.

23. A non-transitory computer-readable recording medium with an executable program stored thereon, the program causing an image processing apparatus to execute:
obtaining each of the first image data and the second image data generated by the multi-layer image sensor according to claim 14;
generating a first interpolation image interpolating the first pixel of the first image sensor and a second interpolation image interpolating the second pixel of the first image sensor, based on the obtained first image data;
generating a third interpolation image interpolating the at least one of the fourth pixel and the fifth pixel of the second image sensor and a fourth interpolation image interpolating the third pixel of the second image sensor, based on the obtained second image data; and
performing color correction of the first interpolation image and the second interpolation image, based on the generated third interpolation image and the generated fourth interpolation image.

\* \* \* \* \*